(12) United States Patent
Hansson et al.

(10) Patent No.: US 7,019,194 B2
(45) Date of Patent: Mar. 28, 2006

(54) SCCE MODIFIED TRANSGENIC MAMMALS AND THEIR USE AS MODELS OF HUMAN DISEASE

(76) Inventors: Lennart Hansson, Heymans Vag 13, S-435 43 Pixbo (SE); Torbjörn Egelrud, Generalsgatan 11, S-903 36 Umeå (SE)

( * ) Notice: Subject to any disclaimer, the term of this patent is extended or adjusted under 35 U.S.C. 154(b) by 21 days.

(21) Appl. No.: 10/071,214

(22) Filed: Feb. 11, 2002

(65) Prior Publication Data

US 2003/0066099 A1 Apr. 3, 2003

Related U.S. Application Data

(60) Provisional application No. 60/267,422, filed on Feb. 9, 2001.

(30) Foreign Application Priority Data

Feb. 9, 2001 (DK) .................................... 2001 00218

(51) Int. Cl.
*A01K 67/027* (2006.01)
*G01N 33/00* (2006.01)

(52) U.S. Cl. ................................. 800/18; 800/3; 800/14

(58) Field of Classification Search ................... 800/18, 800/3, 23, 25, 21, 14
See application file for complete search history.

(56) References Cited

U.S. PATENT DOCUMENTS

| 4,083,974 A | 4/1978 | Turi |
| 4,767,612 A | 8/1988 | Hagen et al. |
| 5,834,290 A | 11/1998 | Egelrud et al. |

FOREIGN PATENT DOCUMENTS

| WO | 8841656 | 9/1998 |
| WO | 9602254 | 2/1999 |
| WO | WO 02/44736 | 6/2002 |

OTHER PUBLICATIONS

Wakayama, T., 1998, Full–term development of mice from enucleated oocytes injected with cumulus cell nuclei. Nature, pp. 369–374.*
Vilotte, JL. 1998, Modification and repression of genes expressed in the mammary gland using gene targeting and other technologies. Journal of Mammary Gland Biology and Neoplasia, vol. 3, pp. 351–362.*
Wiley, 1993, Sv40 early–to–later switch involve titrsion of cellular transcriptional repressors. Genes and Development, vol. 7, pp. 2206–2219.*
Tjian, R. 1981, Regulation od viral trasncriptioon and DNA Replication by the SV40 large T antign. Initiation Signals in Viral Gene Expression, Springer–Verlag, pp. 5–24.*
Tanimoto, H., 1997, Proc. Amer. Asooc. For Cancer Res, vol. 38, p. 413, Abstract #2765.*
Mullins, 1993, Hypertension, vol. 22, pp. 630–633.*
Cameron, 1997, Molec. Biotech. vol. 7, pp. 253–265.*
Hammer, 1990, Cell, vol. 63, pp. 1099–1112.*
Mullins, 1996, J. Clin. Invest., vol. 98, pp. S37–S40.*
Hansson et al., *Epidermal Overexpression of Stratum Corneum Chymotryptic Enzyme in Mice: A Model for Chronic Itchy Dermatitis*. The Journal of Investigative Dermatology, vol. 118, No. 3, pp. 444–449, Mar. 2002.
Smith et al., *Tissue–Specific Expression of Kallikrein Family Transgenes in Mice and Rats*, DNA and Cell Biology, vol. 11, No. 5, pp. 345–358, Jun. 1992.
Brattsand, M. & Egelrud, T. Purification, Molecular Cloning, and Expression of a Human Stratum Corneum Trypein-–like Serine Protease with Possible Function in Desquanation. J Biol Chem 274, 30033–30040 (Oct. 15, 1999).
Bäckman, A., Stranden, P., Brattsand, M. Hansson, L. & Egelrud, T. Molecular Cloning and Tissue Expression of the Murine Analog to Human stratum Corneum Chymotryptia Enzyme. *J Invest Dermatol* 113, 152–155 (Aug., 1999).
Chavanas, S. et al. Mutations in SPINKS, Encoding a Serine Protease Inhibitor, Cause Netherton Syndrome, *Nat Genet* 25, 141–142 (Jun., 2000).
Diamandis, E.P., Yousef, G.M., Liu–Ying, L. Magklara, A. & Obiezu, C.V. The New Human Kallikrein gene Family— Implications in Carcinogenesis. *Trends in Endocrinology and Metabolism* 11, 54–60 (2000).
Ekholm, E. & Egelrud, T. The Expression of Stratum Corneum Chymotryptic Enzyme in Human Anagen Hair Follicles: Further Evidence for its Involvement In Desquanation–like Processes. *Br J Dermatol* 139, 565–590 (1998).
Ekholm, I.E., Brattsand, M. & Egelrud, T. Stratum Corneum Tryptic Enzyme in Nortnal Epidermic: a Missing Link in the Desquamation Process? *J. Invest Dermatol* vol. 114 p. 56–63.
Hansson, L. et al. Cloning, Expression, and Characterization of Stratum Corneum Chymotryptic Enzyme. A Skin–Specific Human Serine Proteinase. *J Biol Chem* 289, 19420–19426 (Jul. 29, 1994).
Hägermark, D., Rajka, G. & Berqvist, U. Experimental Itch in Human Skin Elicited by Rat Mast Cell Chymase. *Acta Derm Venerael (Stockh)* 52, 125–128 (1972).

(Continued)

*Primary Examiner*—Joseph Woitach
*Assistant Examiner*—Valarie Bertoglio
(74) *Attorney, Agent, or Firm*—Iver P. Cooper

(57) ABSTRACT

Genetic evidence that an imbalance in the activity of serine proteases can cause severe skin disease has recently been presented. The serine protease SCCE is preferentially expressed in cornifying epithelia. Increased expression of SCCE in psoriasis has previously been reported. Increased SCCE expression also in chronic lesions of atopic dermatitis is described herein. Transgenic mice expressing human SCCE in suprabasal epidermal keratinocytes were found to develop pathological skin changes with increased epidermal thickness, hyperkeratosis, dermal inflammation, and severe pruritus. The results strengthen the idea that SCCE may be involved in the pathogenesis of inflammatory skin diseases, and may offer a new therapeutic target.

17 Claims, 8 Drawing Sheets

OTHER PUBLICATIONS

Figure 1:
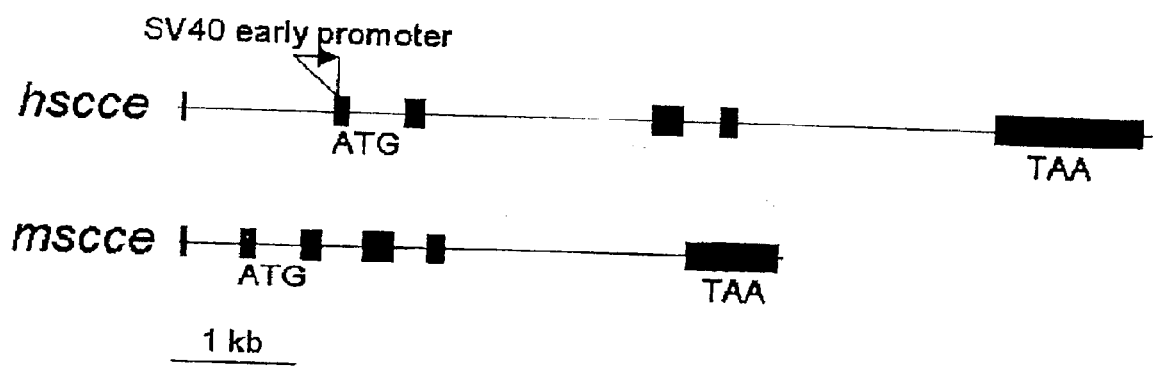

Lindström, P., Bergh A., Holm I., Damber J.E. Expression of Transforming Growth Factor–Beta 1 in Rat Ventral Prostate and Dunning R3327 PAP Prostate Tumor After Castration and Estrogen Treatment. Prostate 29, 209–218 (1996).

Lusky, M. and Botchan M. Inhibition of ev40 Replication in Simlan Cells by Specific pBR322 DNA sequences. *Nature*, 293, 79–81 (1981).

Sondell, B., Thornell, L.E. & Egelrud, T. Evidence That Stratum Corneum Chymotryptic Enzyme is Transported to the Stratum Corneum Extracellular Space Via Larnellar Bodies. *J Invest Dermatol* 104, 819–823 (1995).

Sondell, B., Dyberg, P., Anneroth, G.K., Ostman, P.O. & Egelrud, T. Association Between Expression of Stratum Corneum Chymotryptic Enzyme and Pathological Keratinization in Human Oral Mucosa. *Acta Derm Veneraol (Stockh)* 76, 177–181 (1996).

Vassar et al (1989) Tissue–Specific and Differentiation–Specific Expression of a Human K14 Keratin Gene in Transgenic Mice, Proc Natl Acad Sci U S A.88. 1563–7.

Ekholm, E. & Egelrud, T. Stratum Corneum Chymotryptic Enzyme in Psoriasis. *Arch. Dermatol Res* 291, 195–200 (1999).

Kroon, E., Macdonal, R.J. & Hammer, R.E. The Transcriptional Regulatory Strategy of the Rat Tissue Kallikrein Gene Family. *Genes and Function* 1, 309–310 (1997).

Hägermark, O. Studies on Experimental Itch Induced by Kallikrein and Bradykinin. *Acta Derm Venereol (Stockh)* 54, 397–400 (1974).

Yousef et al. The KLK7 (PRSS6) Gene, Encoding for the Stratum corneum Chymotryptic Enzyme is a New Member of the Human Kallikrein Gene family—Genomic Characterization, Mapping, Tissue Expression and Hormonal Regulation, *Elsevier Biomedical Press*, 254, 119–128 (2000).

Egelrud et al. Epression of Stratum Corneum Chymotryptic Enzyme in Reconstructed Human Epidemis and its Suppression by Retinoic Acid. *Acta dermatovenereologica*, 73, 181–184 (1993).

Tanimoto et al. The stratum corneum Chymotryotic Enzyme That Mediates Shedding and desquamation of Skin cells in Highly Overexpressed in Ovarian Tumor Cells, *Cancer*, 86, 2074–2082 (1999).

Franzke et al. Antileukoprotease Inhibits Stratum Corneum Chymotryptic Enzyme, *Journal of Biomedical Chemistry*, 271, 21886–21890 (Sep. 6, 1996).

* cited by examiner

SEQUENCE LISTING

```
<160> NUMBER OF SEQ ID NOS: 50

<210> SEQ ID NO 1
<211> LENGTH: 986
<212> TYPE: DNA
<213> ORGANISM: Homo sapiens
<220> FEATURE:
<221> NAME/KEY: CDS
<222> LOCATION: (25)..(786)
<223> OTHER INFORMATION:

<400> SEQUENCE: 1
gaattccgcg gatttccggg ctcc atg gca aga tcc ctt ctc ctg ccc ctg         51
              Met Ala Arg Ser Leu Leu Leu Pro Leu
                1               5 cag atc cta ctg cta tcc tta gcc ttg gaa act gca gga gaa gaa gcc        99
Gln Ile Leu Leu Leu Ser Leu Ala Leu Glu Thr Ala Gly Glu Glu Ala
 10              15                  20                  25 cag ggt gac aag att att gat ggc gcc cca tgt gca aga ggc tcc cac       147
Gln Gly Asp Lys Ile Ile Asp Gly Ala Pro Cys Ala Arg Gly Ser His
                 30                  35                  40 cca tgg cag gtg gcc ctg ctc agt ggc aat cag ctc cac tgc gga ggc       195
Pro Trp Gln Val Ala Leu Leu Ser Gly Asn Gln Leu His Cys Gly Gly
             45                  50                  55 gtc ctg gtc aat gag cgc tgg gtg ctc act gcc gcc cac tgc aag atg       243
Val Leu Val Asn Glu Arg Trp Val Leu Thr Ala Ala His Cys Lys Met
         60                  65                  70 aat gag tac acc gtg cac ctg ggc agt gat acg ctg ggc gac agg aga       291
Asn Glu Tyr Thr Val His Leu Gly Ser Asp Thr Leu Gly Asp Arg Arg
     75                  80                  85 gct cag agg atc aag gcc tcg aag tca ttc cgc cac ccc ggc tac tcc       339
Ala Gln Arg Ile Lys Ala Ser Lys Ser Phe Arg His Pro Gly Tyr Ser
 90                  95                 100                 105 aca cag acc cat gtt aat gac ctc atg ctc gtg aag ctc aat agc cag       387
Thr Gln Thr His Val Asn Asp Leu Met Leu Val Lys Leu Asn Ser Gln
                110                 115                 120 gcc agg ctg tca tcc atg gtg aag aaa gtc agg ctg ccc tcc cgc tgc       435
Ala Arg Leu Ser Ser Met Val Lys Lys Val Arg Leu Pro Ser Arg Cys
            125                 130                 135 gaa ccc cct gga acc acc tgt act gtc tcc ggc tgg ggc act acc acg       483
Glu Pro Pro Gly Thr Thr Cys Thr Val Ser Gly Trp Gly Thr Thr Thr
        140                 145                 150 agc cca gat gtg acc ttt ccc tct gac ctc atg tgc gtg gat gtc aag       531
Ser Pro Asp Val Thr Phe Pro Ser Asp Leu Met Cys Val Asp Val Lys
```

-continued

```
            155                 160                 165
ctc atc tcc ccc cag gac tgc acg aag gtt tac aag gac tta ctg gaa    579
Leu Ile Ser Pro Gln Asp Cys Thr Lys Val Tyr Lys Asp Leu Leu Glu
170                 175                 180                 185 aat tcc atg ctg tgc gct ggc atc ccc gac tcc aag aaa aac gcc tgc    627
Asn Ser Met Leu Cys Ala Gly Ile Pro Asp Ser Lys Lys Asn Ala Cys
                190                 195                 200 aat ggt gac tca ggg gga ccg ttg gtg tgc aga ggt acc ctg caa ggt    675
Asn Gly Asp Ser Gly Gly Pro Leu Val Cys Arg Gly Thr Leu Gln Gly
            205                 210                 215 ctg gtg tcc tgg gga act ttc cct tgc ggc caa ccc aat gac cca gga    723
Leu Val Ser Trp Gly Thr Phe Pro Cys Gly Gln Pro Asn Asp Pro Gly
        220                 225                 230 gtc tac act caa gtg tgc aag ttc acc aag tgg ata aat gac acc atg    771
Val Tyr Thr Gln Val Cys Lys Phe Thr Lys Trp Ile Asn Asp Thr Met
    235                 240                 245 aaa aag cat cgc taa cgccacactg agttaattaa ctgtgtgctt ccaacagaaa    826
Lys Lys His Arg
250 atgcacagga gtgaggacgc cgatgaccta tgaagtcaaa tttgacttta cctttcctca    886 aagatatatt taaacctcat gccctgttga taaaccaatc aaattggtaa agacctaaaa    946 ccaaaacaaa taagaaaaca caaaaccctc aacggaattc                          986

<210> SEQ ID NO 2
<211> LENGTH: 253
<212> TYPE: PRT
<213> ORGANISM: Homo sapiens

<400> SEQUENCE: 2

Met Ala Arg Ser Leu Leu Pro Leu Gln Ile Leu Leu Leu Ser Leu
1               5                   10                  15

Ala Leu Glu Thr Ala Gly Glu Glu Ala Gln Gly Asp Lys Ile Ile Asp
            20                  25                  30

Gly Ala Pro Cys Ala Arg Gly Ser His Pro Trp Gln Val Ala Leu Leu
        35                  40                  45

Ser Gly Asn Gln Leu His Cys Gly Gly Val Leu Val Asn Glu Arg Trp
    50                  55                  60

Val Leu Thr Ala Ala His Cys Lys Met Asn Glu Tyr Thr Val His Leu
65                  70                  75                  80

Gly Ser Asp Thr Leu Gly Asp Arg Arg Ala Gln Arg Ile Lys Ala Ser
                85                  90                  95

Lys Ser Phe Arg His Pro Gly Tyr Ser Thr Gln Thr His Val Asn Asp
            100                 105                 110

Leu Met Leu Val Lys Leu Asn Ser Gln Ala Arg Leu Ser Ser Met Val
        115                 120                 125

Lys Lys Val Arg Leu Pro Ser Arg Cys Glu Pro Pro Gly Thr Thr Cys
    130                 135                 140

Thr Val Ser Gly Trp Gly Thr Thr Thr Ser Pro Asp Val Thr Phe Pro
145                 150                 155                 160

Ser Asp Leu Met Cys Val Asp Val Lys Leu Ile Ser Pro Gln Asp Cys
                165                 170                 175

Thr Lys Val Tyr Lys Asp Leu Leu Glu Asn Ser Met Leu Cys Ala Gly
            180                 185                 190

Ile Pro Asp Ser Lys Lys Asn Ala Cys Asn Gly Asp Ser Gly Gly Pro
        195                 200                 205
```

```
Leu Val Cys Arg Gly Thr Leu Gln Gly Leu Val Ser Trp Gly Thr Phe
    210                 215                 220
Pro Cys Gly Gln Pro Asn Asp Pro Gly Val Tyr Thr Gln Val Cys Lys
225                 230                 235                 240
Phe Thr Lys Trp Ile Asn Asp Thr Met Lys Lys His Arg
                245                 250

<210> SEQ ID NO 3
<211> LENGTH: 9729
<212> TYPE: DNA
<213> ORGANISM: Homo sapiens

<400> SEQUENCE: 3
taccacattt tcttaatcca gtctatcact gatggacatt taggttgatt ccctgtgttt       60
gctgttgtca atagttctac aatgaacgta cgtgtccatg tgtctttaaa cagaatgatt     120
tatattcctt tgggtacaca cactgggggct tatgagaggg tggagagtgg gaggaaggag    180
aggatcagaa aaaataact aatgggtact aggcttaata cctgggtgat taaataatct     240
gtataacaaa cccccatggc gcacgttcac ctacgcaaca aacctgcaca tcctgcacat     300
gtaccccga actgaaaagt taaaaaaga aaaataaata tttgcttata aattaataaa       360
tgaagccctc aaaaatgttc tattagataa tgttaagtac agacattttt gttataaata     420
cataatatac aaagaaatct atgtataaca tgattaaaat gaccataaga acatagatcc     480
taaacatggc aaatattagt gggtggggt tagggaaagc gttgttttta acttacacct      540
ctctgttaga gttgggaatg ggttcaggcg taattacagg cacgactggg atcagcttgg     600
acaagttccc ccaggcgggc cagaattagg atgtagggtc taggccaccc ctgagagggg     660
gtgagggcaa gaaaatggcc ccagaagccg ggcgcagtgg ctcacgcctg taatcccagc     720
actttgcggg gccgaggcgg gcacatcatg aggtcaggag atcgagacca ttctggccaa     780
catagtgaaa cccggtctct actaaaaata caaaaattat ctgggagtgg tggtgcgtgc     840
ctgtaatccc aggtactcgg gaggctgagg caggagaatc acttgaacct gggaggcgga     900
gctggcagtg agccgagatc gcgccaccgc actccagcct ggcgatagag agagactcca    960
tccaaaaaaa agaaaggaag ggagggaggg aggaggaag aaagaaagaa aaccgcccca     1020
gagaaggacc cgagccagag cctattctct gagctcagcg actgcttgaa tcccgctcct    1080
gcccctcaga cccagcgcac cgggtccctc ccccgagagc agccaggagg gactgtggga    1140
ccagaatgtg cggggcgca ggagctgggc accgcccgtc cttcggaggg agggtggaga    1200
gagagtgcag tggtgccaat tgctctcgct gcgtcagggt tccagataac cagaaccgca    1260
aatgcaggcg ggggtgtccc agagtcggct ccgcctgcac cccagggcgc tggggccggg    1320
catgggggcgg ggggtgatat aagaggacgg cccagcagag ggctgaagat tttggagccc    1380
agctgtgtgc cagcccaagt cggaacttgg atcacatcag atcctctcga ggtgagaaga    1440
ggcttcatca agggtgcacc tgtaggggag ggggtgatgc tggctccaag cctgactctg    1500
ctctcgagag gtaggggctg cagcctagac tcccggtcct gagcagtgag ggcctggaag    1560
tctgcaattt ggggcctttt agggaaaaac gaactacaga gtcagaagtt tgggttccac    1620
agggaagggc aagatcggag cctagattcc tgggtctcta gggatctgaa gaacaggaat    1680
tttgggtctg agggaggagg ggctgggtt ctggactcct gggtctgagg gaggagggcc    1740
tgggggcctg gactcctggg tctgaggag gaggggctgg gggtctcgac tcctgggtct    1800
gagggaggag gggctggggg cctggactcc tgggtctgag ggaggagggg ctgggaccctg   1860
```

-continued

```
gactcctagg tctgagggag gaggagctgg ggcctggact cctgggtctg agggaggagg    1920
ggctggggcc tggactcctg ggtctgaggg aggatgggct gaggcctaga ctcctgggtc    1980
tgagggagga ggggctgggg cctggactcc tgggtctgag ggaggagggg ctggagcctg    2040
gactcctggg cctgagggag gagggactga gacctggact cctaggtctg agggaggagg    2100
gactgggacc tggactcctg ggtctgaggg aggaggagct gggggcctgg actcctgggt    2160
ctgagggagg cggggctggg ggcctggact cctgggtctg agggaggagg ggttggggcc    2220
tggactcctg agcctgaggg aggagggact tggacctgga ctcctaggtc tgagggagga    2280
ggagctgggg gcctggactc ctaggtctga gggaggaggg gctgggggcc tggactcctg    2340
ggtctgaggg aggaaggtgc tagggtctgg actcttgggt atgagggagg aggaggttag    2400
gggtctggac ttctgagtgt aaggaaggag aggccagaga aaggaatttc tgggtctgag    2460
ggaggagggg ctggggttct ggaccccctag gtctgaggga ggagggggctg gggcctggac    2520
tcctgggtct gtgggggggag gggctgggggc ctggacccct gggtctgagt ggggaggggc    2580
tgggcctgaa tgctttctcc ttctcagctc cagcaggaga ggcccttcct cgcctggcag    2640
cccctgagcg gctcagcagg gcaccatggc aagatccctt ctcctgcccc tgcagatcct    2700
actgctatcc ttagccttgg aaactgcagg agaagaaggt gaaagctgga ctgggaagtc    2760
tgacctcacc tcagggcccc cactgaccct tcccaaggag tccctgagtc agaacccttc    2820
cctcctcaaa cagcttccat cctgggagga ccagactgtc ggctgaagcc cccgctcttc    2880
ctgcttctgc tgactcaggg ggtctctgtc ccctccaggc cctgcctcct gtgctcaggg    2940
tctctctgtg gttccccaga tgagatgcgc ctcctgggtt tctgagtggg ctccttctgt    3000
ctgtctctat ccctatctct tgctttctct gtatttctcc acacatttttc atctgtctct    3060
gtccatctct gactctggga atccctgagg tgcagcctca gccttcccct aatgctagct    3120
acccacatgc tcctccatgt ctccatccag cccagggtga caagattatt gatggcgccc    3180
catgtgcaag aggctcccac ccatggcagg tggccctgct cagtggcaat cagctccact    3240
gcggaggcgt cctggtcaat gagcgctggg tgctcactgc cgcccactgc aagatgaagt    3300
aggtgccacc caagtctctg ctggaggtgc gccagcatct ccagctcgct atgggggtgg    3360
aagggcagtc tttctgtgcc tacggctcta ttctccctctc tctgggtctc tgtcccccctc    3420
tctctgggcc tctgtacccc ctctccctgg ggctctgtcc ccctctctcc ctggctctct    3480
gtctccctct ctctgggtct ctgtcccccct ctctctggat ctctgttccc ctctctctgt    3540
gtctctgtcc cccattctct ctaggtctct gttccccctc ctctctctct gggtctctgt    3600
ccctctctct ctggtctctg tcccccctctc tctctggatc tctgtccccc tctccctggg    3660
cctctgtacc ccctctccct ggggctctgt cccccctctc tgggtctctg tctgcctttc    3720
tctctggatc tctgttcccc tctgtgtctc tgtccccctc tctctctggg tctctgttcc    3780
ccctcctctc tttctgggtc tctgtccctc tctctggg   tctctgtccc cctctctctc    3840
tggtctctgt tcccctcctc tctctctgg  tctctgtccc tctctctctg ggtctctgtc    3900
accctctctc tctgggtctc tgtcaccctc tctctggt   tctgttcccc ctcctctct    3960
ctgtgggtct ctgtccctct ctctgggt   tctgttccc ctctctctct ggtctctgtt    4020
ccccctcctc tctctccgga tctctgtccc ctctccctg gggctctgtc ccctctctc    4080
cctggctctc tgtcttcctc tctgtggggc tctgtccccc tctctctg   gtctctgttc    4140
ccctctctct gggtctctgt ccctctctct ctgggtctct gtccctctct ctctggatct    4200
ctgtccccct ctccctgggc tctgtaccc  cctctccctg gggctctgtc cccctctctc    4260
```

```
tgggtctctg tctgcctttc tctctggatc tctgttcccc tctgtgtctc tgtccccctc    4320
tctctctggg tctctgttcc ccctcctctc tttctgggtc tctgtccctc tctctctggg    4380
tctctgtccc cctctctctc tggtctctgt tcccctcct  ctctctctgg tctctgtccc    4440
tctctctctg gtctctgtc  accctctctc tctgggtctc tgtcaccctc tctctctggt    4500
ctctgttccc cctcctctct ctgtgggtct ctgtccctct ctctctggt  ctctgttccc    4560 ctctctctct ggtctctgtt ccctcctc   tctctccgga tctctgtccc cctctccctg    4620
gggctctgtc ccctctctc  cctggctctc tgtcttcctc tctctgggc  tctgtccccc    4680 tctctctctg gtctctgttc ccctctctct gggtctctgt ccctctctct ctgggtctct    4740
gtccctctct ctctggatct ctgtcccct  ctctctctgg gtctctgttc ccctctctct    4800
gggtctctgt ccctctcct  ctctctgtgt ctctctcccc ctcctctctc tgtgtctctg    4860 tccccctcc  tatctctgtg tctctctccc cctcctctc  tctgggtctc tgtccccccc    4920
tctctgggtc tctgtctccc tctctctggg gctctgtccc cctctctctc tggatctctg    4980
ttcccctctc tctgggtctc tgtctcccct cctctctctg tgtctctgtc ccccctcctc    5040
tctctgggtc tctgtcccca ccccgtcccc caggtctttg cacaccctct ctgtcacagt    5100
gtctcttctg aatctgtgaa tgtcactcct cgcagtgagt acaccgtgca cctgggcagt    5160
gatacgctgg gcgacaggag agctcagagg atcaaggcct cgaagtcatt ccgccacccc    5220
ggctactcca cacagaccca tgttaatgac ctcatgctcg tgaagctcaa tagccaggcc    5280
aggctgtcat ccatggtgaa gaaagtcagg ctgcccctcc gctgcgaacc ccctggaacc    5340
acctgtactg tctccggctg gggcactacc acgagcccag atggtaggtg gcctcagtga    5400
cccaggagtg caggcccag ccctcctccc tcagacccag gagtccaggc ccccagcccc     5460
tcctccctca gacccaggag tccaggcctc agccctcct  ccctcagacc caggagtcca    5520
ggcccccagc cctcctccc  tcagaccgc  gagtccagac cccagcccct cctccctcag    5580
acccagcagt cctgggcccc agaccctcct ccctcggaac caggagcctg aacaacagcc    5640
cttctggtcc tcgcccccat cctctctgac tgacagctct ccctgctcct ccctgcagtg    5700
acctttccct ctgacctcat gtgcgtggat gtcaagctca tctcccccca ggactgcacg    5760
aaggtttaca aggacttact ggaaaattcc atgctgtgcg ctggcatccc cgactccaag    5820
aaaaacgcct gcaatgtgag accctccccc ccaattcctc cccagtcctg gtaccctgt    5880 ctgcatgccc cagggacaga gcttgaccca agtgactggg taccaagccc ggccttgccc    5940
tccccccagg cctggcctcc tcagcttttt ccacctcatt ctctgcctag gtcaggggtg    6000
ggagtttact taggggccga tgtggccctg ggatgggac  agagagttta ataggggtga    6060
gaaagtgggg gtgggaccag ggaaggagac tgaggtgctg gcctcaggcc caaaccctaa    6120
gggggcacca aaaacctcag tgattgagat aaatcataat gcaatattta aaaataaaaa    6180
taaaaactca tgcagaagtc catgatggac aaaatgtcac attttaaata aagagcaggt    6240
ggatcttact gaattttccc ttgccgtaag tactagcgtg gctcagcaca gcgctgtact    6300
ggcactgtct tcatttaaaa tgtggatacc atgcccatca tgcagtttta tgtattacat    6360
ttgatttcgt taagtactgc attgaagtat tgtgtattgc agttactgag attttgtgcc    6420
tgaagctgat gactcactca cctgaccctg gccctggtcc cggggaaaac actctttctc    6480
tccacctcct ctctgttccc tctttctggc cttttgtcat ccctctgtt  tctgaacagt    6540 cttcccacat ctctctttgt gacataattt catttcattc ttttcctctt tgtttttct    6600
```

```
ctgtgttgag ctagcttgct ctccctccct tgttctctct ccatgccctc ctctctgctc    6660
tctgtcttct ccctctttct cttgcttctc tctctctcct ccctccctc tctcctctcc     6720 ctgcccccct gctctctctt ttttcctctc tctctgtctc ctctctggcc ctctcctctt    6780
tctctctctc ccccacttct ctgtctctct tcatctctct ccctcatctc tccttgcccc    6840
ctccttttta ctgtctctct cttttctcttt cttctatctc tctcctctcc ccgccgctcc   6900
cccatctctg tctttctttc tctctcttta ttctcctcct ctcttccagt ctctctctcc    6960
tctccccacc cccacccat  ctctctcccc acaccttccc cccctttctc tttgtctctc    7020
tcttctacct ctttcttctc cacccccatc tctctctctc ttctcttccc acaccctccc    7080
catctccctc atctctttgt ctgtctctct tctccctcct tcttttccac ccccatctct    7140
ctgtctctct ctctccccat accctttccc tcttcctcat ctctctttgt ctctctctcc    7200
tttccctctt tcttctccac ctccaactct ctctgtctct ccacacccat cctccttgct    7260
cacatctgca ccttcagctg tcaggggatg tgggatggtg agtgttaggg atagaggaga    7320
tgggagagag atgactgtcc tagagaatag ggtgttcccc ttctcccctg gtgagggcca    7380
gtttcatgaa tgtgcaagct ctgcacggac acagagcccc acactcagaa gggtctcaaa    7440
cttagtctaa tgcattcctg ctgttgtctt gaaattctca ataatttttg aacaaagggc    7500
cctgcatttt cgttttgcac caagtcctgt aaattatgta actggtcttc accctggtct    7560
ccgagaccat cgtgtccccc tttcctgcgc acagggcac  gcatccaccc cttggagatg    7620
atgttccttc tcccactagc ttggagcagg gtccttaaca ttggaaaata aagagtgctc    7680
tgatcctgga agccccaccc cttctctgca attggtctca ttggccaagg gtcaaaccag    7740
tgtcttcaaa ggacctagtg tgtccctagc actagctctc ccattagtcc ccagagacaa    7800
tgagtctctt ctcattggct atggtggaag tccataatct gcaagacaaa gaccgataac    7860
tgaggaatgt atgagaatga gttgggcttt gatctgaagc caaagttaat ctccggctct    7920
attccctcta gggtgactca gggggaccgt tggtgtgcag aggtaccctg caaggtctgg    7980
tgtcctgggg aactttccct tgcggccaac ccaatgaccc aggagtctac actcaagtgt    8040
gcaagttcac caagtggata aatgacacca tgaaaaagca tcgctaacgc cacactgagt    8100
taattaactg tgtgcttcca acagaaaatg cacaggagtg aggacgccga tgacctatga    8160
agtcaaattt gactttacct ttcctcaaag atatatttaa acctcatgcc ctgttgataa    8220
accaatcaaa ttggtaaaga cctaaaacca aacaaataa  agaaacacaa aaccctcagt    8280
gctggagaag agtcagtgag accagcactc tcaaacactg gaactggacg ttcgtacagt    8340
ctttacggaa gacacttggt caacgtacac cgagaccctt attcaccacc tttgacccag    8400
taactctaat cttaggaaga acctactgaa acaaaaaaa  tccaaaatgt agaacaagac    8460
ttgaatttac catgatatta tttatcacag aaatgaagtg aaaccatcaa acatgttcca    8520
aaagtaccag atggcttaaa taatagtctg gcttggcaca acgatgtttt ttttctttga    8580
gacagagtct ctgttgcttg ggctgcaatg cagtgatgca atcttggctc actgcaacct    8640
ccgcctcctg ggttcaagtg attctcgtgc ttcagcctcc caagtacctg ggactacagg    8700
tgtgcaccac cacaccaggc taattttttg tgtattttta ctagagacag ggtttcacca    8760
tgttggccag cgtggtcttg aacgcctgac ctcagatgat ccaccacct  tggcctccca    8820 aagtgctggg attacaggca tgagccacca cggccagccc acaatgatat tacaaaccta    8880
ttaaaaatga tacttagaca gaattgtcag tattattcaa gaacatttag gctataggat    8940
gttaaatgac aaaaggaagg acaaaaatat atatgtatgt gaccctaccc ataaaaaatg    9000
```

```
aaatattcac agaatcagat ctgaaaacac atgtcccaga ctgcatactg gggtcgtcat    9060
gaggtgtctc cttccttctg tgtactttc cttgaatgtg cactttata acatgaaaaa     9120 taaaggtggg gaaaaaagtc tgaagatcta agattggaga gaggtgacct ttcaggaagg    9180
gagactagaa agaaatatgt gcctggtttt gagccctggt cctgccggcc ctgttccagg    9240
gcatatttcc atttcccaga tctcagtttt tcctgtctgt aaaatgggag agagaggaaa    9300
ggatggagag aggaagaagg aagggaggag ggaggagaga acaggccaac ttcatcagcg    9360
tgggaagggg tgtgaaagtg tttctgagca tctcacgagt gacaagtgag gagggaggct    9420
ggcggttttc agagggattg ggatgacagt agacaggaca caggggtccc acagggtct     9480 gccagaagta agcaaacagt gccggaggaa gatggtggca cctgctcccc aagaagggag    9540
ggaaaggaac ctcgggaagc gggtaggatg agggaggagt cctctgtgac tcagagcctg    9600
gccacagccc cagccatcta acatcaaaga tcctctgtgt ggtcacacct cagacgctgc    9660
tgaccgagga gccactccag cccaggacac gccctcctac ctgttcttcc tgtttttctc    9720
ccagaattc                                                           9729
```

```
<210> SEQ ID NO 4
<211> LENGTH: 23
<212> TYPE: PRT
<213> ORGANISM: Bos Taurus

<400> SEQUENCE: 4

Ala Gly Ile Pro Asn Ser Arg Thr Asn Ala Cys Asn Gly Asp Ser Gly
1               5                   10                  15

Gly Pro Leu Met Cys Lys Gly
            20

<210> SEQ ID NO 5
<211> LENGTH: 23
<212> TYPE: PRT
<213> ORGANISM: Sus scrofa

<400> SEQUENCE: 5

Ala Gly Ile Pro Asn Ser Lys Thr Asn Ala Cys Asn Gly Asp Ser Gly
1               5                   10                  15

Gly Pro Leu Val Cys Lys Gly
            20

<210> SEQ ID NO 6
<211> LENGTH: 23
<212> TYPE: PRT
<213> ORGANISM: Homo sapiens

<400> SEQUENCE: 6

Ala Gly Ile Pro Asp Ser Lys Lys Asn Ala Cys Asn Gly Asp Ser Gly
1               5                   10                  15

Gly Pro Leu Val Cys Arg Gly
            20

<210> SEQ ID NO 7
<211> LENGTH: 23
<212> TYPE: PRT
<213> ORGANISM: Rattus norvegicus

<400> SEQUENCE: 7

Ala Gly Ile Pro Asp Ser Lys Thr Asn Thr Cys Asn Gly Asp Ser Gly
1               5                   10                  15
```

-continued

```
Gly Pro Leu Val Cys Asn Asp
         20

<210> SEQ ID NO 8
<211> LENGTH: 23
<212> TYPE: PRT
<213> ORGANISM: Mus musculus

<400> SEQUENCE: 8

Ala Gly Ile Pro Asp Ser Lys Thr Asn Thr Cys Asn Gly Asp Ser Gly
1               5                   10                  15

Gly Pro Leu Val Cys Asn Asp
         20

<210> SEQ ID NO 9
<211> LENGTH: 38
<212> TYPE: PRT
<213> ORGANISM: Bos Taurus

<400> SEQUENCE: 9

Gln Glu Asp Gln Gly Asn Lys Ser Gly Glu Lys Ile Ile Asp Gly Val
1               5                   10                  15

Pro Cys Pro Arg Gly Ser Gln Pro Trp Gln Val Ala Leu Leu Lys Gly
            20                  25                  30

Ser Gln Leu His Cys Gly
        35

<210> SEQ ID NO 10
<211> LENGTH: 37
<212> TYPE: PRT
<213> ORGANISM: Sus scrofa

<400> SEQUENCE: 10

Gln Glu Gly Gln Asp Lys Ser Gly Glu Lys Ile Ile Asp Gly Val Pro
1               5                   10                  15

Cys Pro Gly Gly Ser Arg Pro Trp Gln Val Ala Leu Leu Lys Gly Asn
            20                  25                  30

Gln Leu His Cys Gly
        35

<210> SEQ ID NO 11
<211> LENGTH: 34
<212> TYPE: PRT
<213> ORGANISM: Homo sapiens

<400> SEQUENCE: 11

Glu Glu Ala Gln Gly Asp Lys Ile Ile Asp Gly Ala Pro Cys Ala Arg
1               5                   10                  15

Gly Ser His Pro Trp Gln Val Ala Leu Leu Ser Gly Asn Gln Leu His
            20                  25                  30

Cys Gly

<210> SEQ ID NO 12
<211> LENGTH: 31
<212> TYPE: PRT
<213> ORGANISM: Rattus norvegicus

<400> SEQUENCE: 12

Gln Gly Glu Arg Ile Ile Asp Gly Tyr Lys Cys Lys Glu Gly Ser His
1               5                   10                  15
```

```
Pro Trp Gln Val Ala Leu Leu Lys Gly Asp Gln Leu His Cys Gly
            20                  25                  30
```

<210> SEQ ID NO 13
<211> LENGTH: 31
<212> TYPE: PRT
<213> ORGANISM: Mus musculus

<400> SEQUENCE: 13

```
Gln Gly Glu Arg Ile Ile Asp Gly Ile Lys Cys Lys Glu Gly Ser His
1               5                   10                  15

Pro Trp Gln Val Ala Leu Leu Lys Gly Asn Gln Leu His Cys Gly
            20                  25                  30
```

<210> SEQ ID NO 14
<211> LENGTH: 7
<212> TYPE: PRT
<213> ORGANISM: Artificial Sequence
<220> FEATURE:
<223> OTHER INFORMATION: Consensus sequence for cleavage site in
      C-terminal of SCCE.
<220> FEATURE:
<221> NAME/KEY: misc_feature
<222> LOCATION: (2)..(2)
<223> OTHER INFORMATION: Xaa is either aspartate (Asp) or glutamate (Glu)
<220> FEATURE:
<221> NAME/KEY: misc_feature
<222> LOCATION: (3)..(3)
<223> OTHER INFORMATION: Xaa is either lysine (Lys) or arginine (Arg)

<400> SEQUENCE: 14

```
Gly Xaa Xaa Ile Ile Asp Gly
1               5
```

<210> SEQ ID NO 15
<211> LENGTH: 8
<212> TYPE: PRT
<213> ORGANISM: Artificial Sequence
<220> FEATURE:
<223> OTHER INFORMATION: Consensus of the substrate specificity pouch
<220> FEATURE:
<221> NAME/KEY: misc_feature
<222> LOCATION: (1)..(1)
<223> OTHER INFORMATION: Xaa is any amino acid residue
<220> FEATURE:
<221> NAME/KEY: misc_feature
<222> LOCATION: (3)..(3)
<223> OTHER INFORMATION: Xaa is any amino acid residue
<220> FEATURE:
<221> NAME/KEY: misc_feature
<222> LOCATION: (4)..(4)
<223> OTHER INFORMATION: Xaa is Cys
<220> FEATURE:
<221> NAME/KEY: misc_feature
<222> LOCATION: (5)..(5)
<223> OTHER INFORMATION: Xaa is any amino acid residue
<220> FEATURE:
<221> NAME/KEY: misc_feature
<222> LOCATION: (6)..(6)
<223> OTHER INFORMATION: Xaa is Gly
<220> FEATURE:
<221> NAME/KEY: misc_feature
<222> LOCATION: (7)..(7)
<223> OTHER INFORMATION: Xaa is Asp

<400> SEQUENCE: 15

```
Xaa Asn Xaa Xaa Xaa Xaa Xaa Ser
1               5
```

<210> SEQ ID NO 16
<211> LENGTH: 20

```
<212> TYPE: DNA
<213> ORGANISM: Artificial Sequence
<220> FEATURE:
<223> OTHER INFORMATION: PCR primer SYM3300

<400> SEQUENCE: 16
ggtggccctg ctcagtggca                                            20

<210> SEQ ID NO 17
<211> LENGTH: 22
<212> TYPE: DNA
<213> ORGANISM: Artificial Sequence
<220> FEATURE:
<223> OTHER INFORMATION: PCR primer SYM3301

<400> SEQUENCE: 17
caccatggat gacacagcct gg                                         22

<210> SEQ ID NO 18
<211> LENGTH: 20
<212> TYPE: DNA
<213> ORGANISM: Artificial Sequence
<220> FEATURE:
<223> OTHER INFORMATION: PCR primer SYM3302

<400> SEQUENCE: 18
aataaagaaa cacaaaaccc                                            20

<210> SEQ ID NO 19
<211> LENGTH: 18
<212> TYPE: DNA
<213> ORGANISM: Artificial Sequence
<220> FEATURE:
<223> OTHER INFORMATION: PCR primer SYM3418

<400> SEQUENCE: 19
tgtaatatca ttgtgggc                                              18

<210> SEQ ID NO 20
<211> LENGTH: 18
<212> TYPE: DNA
<213> ORGANISM: Artificial Sequence
<220> FEATURE:
<223> OTHER INFORMATION: PCR primer SYM4118

<400> SEQUENCE: 20
ggatgtgaag ctcatctc                                              18

<210> SEQ ID NO 21
<211> LENGTH: 18
<212> TYPE: DNA
<213> ORGANISM: Artificial Sequence
<220> FEATURE:
<223> OTHER INFORMATION: PCR primer SYM4121

<400> SEQUENCE: 21
tggagtcggg gatgccag                                              18

<210> SEQ ID NO 22
<211> LENGTH: 25
<212> TYPE: DNA
<213> ORGANISM: Artificial Sequence
<220> FEATURE:
<223> OTHER INFORMATION: PCR primer SYM4720

<400> SEQUENCE: 22
```

```
gggagggtgg agagagagtg cagtg                                                  25
```

<210> SEQ ID NO 23
<211> LENGTH: 21
<212> TYPE: DNA
<213> ORGANISM: Artificial Sequence
<220> FEATURE:
<223> OTHER INFORMATION: PCR primer SYM4899

<400> SEQUENCE: 23

```
agtctaggct gcagccccta c                                                      21
```

<210> SEQ ID NO 24
<211> LENGTH: 22
<212> TYPE: DNA
<213> ORGANISM: Artificial Sequence
<220> FEATURE:
<223> OTHER INFORMATION: PCR primer hEXON1

<400> SEQUENCE: 24

```
ctcgagggat ctgatgtgat cc                                                     22
```

<210> SEQ ID NO 25
<211> LENGTH: 24
<212> TYPE: DNA
<213> ORGANISM: Artificial Sequence
<220> FEATURE:
<223> OTHER INFORMATION: PCR primer mEXON1

<400> SEQUENCE: 25

```
ctgggagtga cttggcgtgg ctct                                                   24
```

<210> SEQ ID NO 26
<211> LENGTH: 23
<212> TYPE: DNA
<213> ORGANISM: Artificial Sequence
<220> FEATURE:
<223> OTHER INFORMATION: PCR primer specific for human SCCE IE2

<400> SEQUENCE: 26

```
gctctcccat tagtccccag aga                                                    23
```

<210> SEQ ID NO 27
<211> LENGTH: 24
<212> TYPE: DNA
<213> ORGANISM: Artificial Sequence
<220> FEATURE:
<223> OTHER INFORMATION: PCR primer specific for human SCEE MJ2

<400> SEQUENCE: 27

```
ccacttggtg aacttgcaca cttg                                                   24
```

<210> SEQ ID NO 28
<211> LENGTH: 18
<212> TYPE: DNA
<213> ORGANISM: Artificial Sequence
<220> FEATURE:
<223> OTHER INFORMATION: Forward primer covering the position 427-444 of
      the human SCCE cDNA sequence.

<400> SEQUENCE: 28

```
gcgaaccccc tggaacaa                                                          18
```

<210> SEQ ID NO 29
<211> LENGTH: 21
<212> TYPE: DNA

```
<213> ORGANISM: Artificial Sequence
<220> FEATURE:
<223> OTHER INFORMATION: Reverse primer covering the position 490-510 of
      the human cDNA sequence in exon five.

<400> SEQUENCE: 29
acatccacgc acatgaggtc a                                               21

<210> SEQ ID NO 30
<211> LENGTH: 29
<212> TYPE: DNA
<213> ORGANISM: Artificial Sequence
<220> FEATURE:
<223> OTHER INFORMATION: The real time amplification probe covering the
      position 445-473 of the human cDNA sequence in exon four.

<400> SEQUENCE: 30
cctgtactgt ctccggctgg ggcactacc                                       29

<210> SEQ ID NO 31
<211> LENGTH: 25
<212> TYPE: DNA
<213> ORGANISM: Artificial Sequence
<220> FEATURE:
<223> OTHER INFORMATION: PCR primer mS3

<400> SEQUENCE: 31
caaggagaaa ggattataga tggct                                           25

<210> SEQ ID NO 32
<211> LENGTH: 21
<212> TYPE: DNA
<213> ORGANISM: Artificial Sequence
<220> FEATURE:
<223> OTHER INFORMATION: PCR primer 698

<400> SEQUENCE: 32
aaggctccgc acccatggca g                                               21

<210> SEQ ID NO 33
<211> LENGTH: 26
<212> TYPE: DNA
<213> ORGANISM: Artificial Sequence
<220> FEATURE:
<223> OTHER INFORMATION: PCR primer 696

<400> SEQUENCE: 33
tgcaatggtg actcagggg gccctt                                           26

<210> SEQ ID NO 34
<211> LENGTH: 23
<212> TYPE: DNA
<213> ORGANISM: Artificial Sequence
<220> FEATURE:
<223> OTHER INFORMATION: PCR primer H2

<400> SEQUENCE: 34
gacccaggcg tctacactca agt                                             23

<210> SEQ ID NO 35
<211> LENGTH: 25
<212> TYPE: DNA
<213> ORGANISM: Artificial Sequence
<220> FEATURE:
<223> OTHER INFORMATION: PCR primer mS4

<400> SEQUENCE: 35
```

```
gagaccatga aacccatcg ctaac                                              25

<210> SEQ ID NO 36
<211> LENGTH: 26
<212> TYPE: DNA
<213> ORGANISM: Artificial Sequence
<220> FEATURE:
<223> OTHER INFORMATION: PCR primer KO 0905

<400> SEQUENCE: 36
tgactttctt cacactggac gacagc                                            26

<210> SEQ ID NO 37
<211> LENGTH: 26
<212> TYPE: DNA
<213> ORGANISM: Artificial Sequence
<220> FEATURE:
<223> OTHER INFORMATION: PCR primer GR 0905

<400> SEQUENCE: 37
cttcacactg gctgatagcc tggccg                                            26

<210> SEQ ID NO 38
<211> LENGTH: 28
<212> TYPE: DNA
<213> ORGANISM: Artificial Sequence
<220> FEATURE:
<223> OTHER INFORMATION: PCR primer Ngr

<400> SEQUENCE: 38
cagggtggcg gaatgacctc atggccct                                          28

<210> SEQ ID NO 39
<211> LENGTH: 28
<212> TYPE: DNA
<213> ORGANISM: Artificial Sequence
<220> FEATURE:
<223> OTHER INFORMATION: PCR primer RA 1016

<400> SEQUENCE: 39
ctactccaca aggacccatg tcaatgac                                          28

<210> SEQ ID NO 40
<211> LENGTH: 28
<212> TYPE: DNA
<213> ORGANISM: Artificial Sequence
<220> FEATURE:
<223> OTHER INFORMATION: PCR primer nRA 1016

<400> SEQUENCE: 40
gctgtgtgct ggcattcccg actctaag                                          28

<210> SEQ ID NO 41
<211> LENGTH: 30
<212> TYPE: DNA
<213> ORGANISM: Artificial Sequence
<220> FEATURE:
<223> OTHER INFORMATION: SMART II oligonucleotide

<400> SEQUENCE: 41
aagcagtggt aacaacgcag agtacgcggg                                        30

<210> SEQ ID NO 42
<211> LENGTH: 27
<212> TYPE: DNA
```

```
<213> ORGANISM: Artificial Sequence
<220> FEATURE:
<223> OTHER INFORMATION: 5'-RACE cDNA synthesis primer
<220> FEATURE:
<221> NAME/KEY: misc_feature
<222> LOCATION: (27)..(27)
<223> OTHER INFORMATION: n is a or g or c or t

<400> SEQUENCE: 42
tttttttttt tttttttttt tttttvn                                      27

<210> SEQ ID NO 43
<211> LENGTH: 45
<212> TYPE: DNA
<213> ORGANISM: Artificial Sequence
<220> FEATURE:
<223> OTHER INFORMATION: Long universal primer

<400> SEQUENCE: 43
ctaatacgac tcactatagg gcaagcagtg gtaacaacgc agagt                  45

<210> SEQ ID NO 44
<211> LENGTH: 23
<212> TYPE: DNA
<213> ORGANISM: Artificial Sequence
<220> FEATURE:
<223> OTHER INFORMATION: Short universal primer

<400> SEQUENCE: 44
ctaatacgac tcactatagg gcc                                          23

<210> SEQ ID NO 45
<211> LENGTH: 23
<212> TYPE: DNA
<213> ORGANISM: Artificial Sequence
<220> FEATURE:
<223> OTHER INFORMATION: Nested universal primer

<400> SEQUENCE: 45
aagcagtggt aacaacgcag agt                                          23

<210> SEQ ID NO 46
<211> LENGTH: 243
<212> TYPE: PRT
<213> ORGANISM: Artificial Sequence
<220> FEATURE:
<223> OTHER INFORMATION: Deduced amino acid sequence from the C-terminal
      part of SCCE from cow.

<400> SEQUENCE: 46

Met Thr Thr Pro Leu Val Ile Leu Leu Thr Phe Ala Leu Gly Ser
1               5                   10                  15

Val Ala Gln Glu Asp Gln Gly Asn Lys Ser Gly Glu Lys Ile Ile Asp
            20                  25                  30

Gly Val Pro Cys Pro Arg Gly Ser Gln Pro Trp Gln Val Ala Leu Leu
        35                  40                  45

Lys Gly Ser Gln Leu His Cys Gly Gly Val Leu Leu Asn Glu Gln Trp
    50                  55                  60

Val Leu Thr Ala Ala His Cys Met Asn Glu Tyr Asn Val His Met Gly
65                  70                  75                  80

Ser Val Arg Leu Val Gly Gly Gln Lys Ile Lys Ala Thr Arg Ser Phe
                85                  90                  95

Arg His Pro Gly Tyr Ser Thr Gln Thr His Ala Asn Asp Leu Met Leu
            100                 105                 110
```

-continued

```
Val Lys Leu Asn Gly Arg Ala Lys Leu Ser Ser Val Lys Val
        115                 120                 125

Asn Leu Pro Ser His Cys Asp Pro Gly Thr Met Cys Thr Val Ser
        130                 135                 140

Gly Trp Gly Thr Thr Thr Ser Pro Asp Val Thr Phe Pro Gly Gln Leu
145                 150                 155                 160

Met Cys Thr Asp Val Lys Leu Ile Ser Pro Gln Asp Cys Arg Lys Val
                    165                 170                 175

Tyr Lys Asp Leu Leu Gly Asp Ser Met Leu Cys Ala Gly Ile Pro Asn
                180                 185                 190

Ser Arg Thr Asn Ala Cys Asn Gly Asp Ser Gly Gly Pro Leu Met Cys
            195                 200                 205

Lys Gly Thr Leu Gln Gly Val Val Ser Trp Gly Ser Phe Pro Cys Gly
        210                 215                 220

Gln Pro Asn Asp Pro Gly Val Tyr Thr Gln Val Cys Lys Tyr Val Asn
225                 230                 235                 240

Trp Ile Lys
```

<210> SEQ ID NO 47
<211> LENGTH: 249
<212> TYPE: PRT
<213> ORGANISM: Artificial Sequence
<220> FEATURE:
<223> OTHER INFORMATION: Deduced amino acid sequence from the C-terminal
      part of SCCE from pig.

<400> SEQUENCE: 47

```
Met Ala Arg Pro Leu Leu Pro Pro Arg Leu Ile Leu Leu Leu Ser Leu
1               5                   10                  15

Ala Leu Gly Ser Ala Ala Gln Glu Gly Gln Asp Lys Ser Gly Glu Lys
                20                  25                  30

Ile Ile Asp Gly Val Pro Cys Pro Gly Gly Ser Arg Pro Trp Gln Val
            35                  40                  45

Ala Leu Leu Lys Gly Asn Gln Leu His Cys Gly Gly Val Leu Val Asn
        50                  55                  60

Gln Gln Trp Val Leu Thr Ala Ala His Cys Met Met Asn Asp Tyr Asn
65                  70                  75                  80

Val His Leu Gly Ser Asp Arg Leu Asp Asp Arg Lys Gly Gln Lys Ile
                85                  90                  95

Arg Ala Met Arg Ser Phe Arg His Pro Gly Tyr Ser Thr Gln Thr His
                100                 105                 110

Val Asn Asp Leu Met Leu Val Lys Leu Ser Arg Pro Ala Arg Leu Ser
            115                 120                 125

Ala Ser Val Lys Lys Val Asn Leu Pro Ser Arg Cys Glu Pro Pro Gly
        130                 135                 140

Thr Thr Cys Thr Val Ser Gly Trp Gly Thr Thr Thr Ser Pro Asp Val
145                 150                 155                 160

Thr Phe Pro Ala Asp Leu Met Cys Thr Asp Val Lys Leu Ile Ser Ser
                165                 170                 175

Gln Asp Cys Lys Lys Val Tyr Lys Asp Leu Leu Gly Ser Ser Met Leu
                180                 185                 190

Cys Ala Gly Ile Pro Asn Ser Lys Thr Asn Ala Cys Asn Gly Asp Ser
            195                 200                 205

Gly Gly Pro Leu Val Cys Lys Gly Thr Leu Gln Gly Leu Val Ser Trp
        210                 215                 220
```

```
Gly Thr Phe Pro Cys Gly Gln Pro Asn Asp Pro Gly Val Tyr Thr Gln
225                 230                 235                 240

Val Cys Lys Tyr Ile Asp Trp Ile Asn
                245

<210> SEQ ID NO 48
<211> LENGTH: 253
<212> TYPE: PRT
<213> ORGANISM: Artificial Sequence
<220> FEATURE:
<223> OTHER INFORMATION: Deduced amino acid sequence from the C-terminal
      part of SCCE from homo sapiens.

<400> SEQUENCE: 48

Met Ala Arg Ser Leu Leu Pro Leu Gln Ile Leu Leu Ser Leu
1               5                   10                  15

Ala Leu Glu Thr Ala Gly Glu Glu Ala Gln Gly Asp Lys Ile Ile Asp
            20                  25                  30

Gly Ala Pro Cys Ala Arg Gly Ser His Pro Trp Gln Val Ala Leu Leu
        35                  40                  45

Ser Gly Asn Gln Leu His Cys Gly Gly Val Leu Val Asn Glu Arg Trp
    50                  55                  60

Val Leu Thr Ala Ala His Cys Lys Met Asn Glu Tyr Thr Val His Leu
65                  70                  75                  80

Gly Ser Asp Thr Leu Gly Asp Arg Arg Ala Gln Arg Ile Lys Ala Ser
                85                  90                  95

Lys Ser Phe Arg His Pro Gly Tyr Ser Thr Gln Thr His Val Asn Asp
            100                 105                 110

Leu Met Leu Val Lys Leu Asn Ser Gln Ala Arg Leu Ser Ser Met Val
        115                 120                 125

Lys Lys Val Arg Leu Pro Ser Arg Cys Glu Pro Pro Gly Thr Thr Cys
    130                 135                 140

Thr Val Ser Gly Trp Gly Thr Thr Thr Ser Pro Asp Val Thr Phe Pro
145                 150                 155                 160

Ser Asp Leu Met Cys Val Asp Val Lys Leu Ile Ser Pro Gln Asp Cys
                165                 170                 175

Thr Lys Val Tyr Lys Asp Leu Leu Glu Asn Ser Met Leu Cys Ala Gly
            180                 185                 190

Ile Pro Asp Ser Lys Lys Asn Ala Cys Asn Gly Asp Ser Gly Gly Pro
        195                 200                 205

Leu Val Cys Arg Gly Thr Leu Gln Gly Leu Val Ser Trp Gly Thr Phe
    210                 215                 220

Pro Cys Gly Gln Pro Asn Asp Pro Gly Val Tyr Thr Gln Val Cys Lys
225                 230                 235                 240

Phe Thr Lys Trp Ile Asn Asp Thr Met Lys Lys His Arg
                245                 250

<210> SEQ ID NO 49
<211> LENGTH: 226
<212> TYPE: PRT
<213> ORGANISM: Artificial Sequence
<220> FEATURE:
<223> OTHER INFORMATION: Deduced amino acid sequence from the C-terminal
      part of SCCE from rat.

<400> SEQUENCE: 49

Met Gly Val Trp Leu Leu Ser Leu Leu Thr Val Leu Leu Ser Leu Ala
1               5                   10                  15
```

-continued

```
Leu Glu Thr Ala Gly Gln Gly Glu Arg Ile Ile Asp Gly Tyr Lys Cys
            20                  25                  30

Lys Glu Gly Ser His Pro Trp Gln Val Ala Leu Leu Lys Gly Asp Gln
        35                  40                  45

Leu His Cys Gly Gly Val Leu Val Gly Glu Ser Trp Val Leu Thr Ala
    50                  55                  60

Ala His Cys Lys Met Gly Gln Tyr Thr Val His Leu Gly Ser Asp Lys
65                  70                  75                  80

Ile Glu Asp Gln Ser Ala Gln Arg Ile Lys Ala Ser Arg Ser Phe Arg
                85                  90                  95

His Pro Gly Tyr Ser Thr Arg Thr His Val Asn Asp Ile Met Leu Val
            100                 105                 110

Lys Met Asp Lys Pro Val Lys Met Ser Asp Lys Val Gln Lys Val Lys
        115                 120                 125

Leu Pro Asp His Cys Glu Pro Pro Gly Thr Leu Cys Thr Val Ser Gly
    130                 135                 140

Trp Gly Thr Thr Thr Ser Pro Asp Val Thr Phe Pro Ser Asp Leu Met
145                 150                 155                 160

Cys Ser Asp Val Lys Leu Ile Ser Ser Gln Glu Cys Lys Lys Val Tyr
                165                 170                 175

Lys Asp Leu Leu Gly Lys Thr Met Leu Cys Ala Gly Ile Pro Asp Ser
            180                 185                 190

Lys Thr Asn Thr Cys Asn Gly Asp Ser Gly Gly Pro Leu Val Cys Asn
        195                 200                 205

Asp Thr Leu Gln Gly Leu Val Ser Trp Gly Thr Tyr Pro Cys Gly Gln
    210                 215                 220

Pro Asn
225
```

<210> SEQ ID NO 50
<211> LENGTH: 249
<212> TYPE: PRT
<213> ORGANISM: Artificial Sequence
<220> FEATURE:
<223> OTHER INFORMATION: Deduced amino acid sequence from the C-terminal
      part of SCCE from mouse.

<400> SEQUENCE: 50

```
Met Gly Val Trp Leu Leu Ser Leu Ile Thr Val Leu Leu Ser Leu Ala
1               5                   10                  15

Leu Glu Thr Ala Gly Gln Gly Glu Arg Ile Ile Asp Gly Ile Lys Cys
            20                  25                  30

Lys Glu Gly Ser His Pro Trp Gln Val Ala Leu Leu Lys Gly Asn Gln
        35                  40                  45

Leu His Cys Gly Gly Val Leu Val Asp Lys Tyr Trp Val Leu Thr Ala
    50                  55                  60

Ala His Cys Lys Met Gly Gln Tyr Gln Val Gln Leu Gly Ser Asp Lys
65                  70                  75                  80

Ile Gly Asp Gln Ser Ala Gln Lys Ile Lys Ala Thr Lys Ser Phe Arg
                85                  90                  95

His Pro Gly Tyr Ser Thr Lys Thr His Val Asn Asp Ile Met Leu Val
            100                 105                 110

Arg Leu Asp Glu Pro Val Lys Met Ser Ser Lys Val Glu Ala Val Gln
        115                 120                 125

Leu Pro Glu His Cys Glu Pro Pro Gly Thr Ser Cys Thr Val Ser Gly
```

-continued

```
            130                 135                 140
Trp Gly Thr Thr Thr Ser Pro Asp Val Thr Phe Pro Ser Asp Leu Met
145                 150                 155                 160

Cys Ser Asp Val Lys Leu Ile Ser Ser Arg Glu Cys Lys Lys Val Tyr
                165                 170                 175

Lys Asp Leu Leu Gly Lys Thr Met Leu Cys Ala Gly Ile Pro Asp Ser
            180                 185                 190

Lys Thr Asn Thr Cys Asn Gly Asp Ser Gly Gly Pro Leu Val Cys Asn
            195                 200                 205

Asp Thr Leu Gln Gly Leu Ala Ser Arg Gly Thr Tyr Pro Cys Gly Gln
210                 215                 220

Pro Asn Asp Pro Gly Val Tyr Thr Gln Val Cys Lys Tyr Lys Arg Trp
225                 230                 235                 240

Val Met Glu Thr Met Lys Thr His Arg
                245
```

SCCE MODIFIED TRANSGENIC MAMMALS AND THEIR USE AS MODELS OF HUMAN DISEASE

This application is a nonprovisional of U.S. provisional application Ser. No. 60/267,422, filed Feb. 9, 2001, which is hereby incorporated by reference in its entirety. All patent and nonpatent references cited in that application, or in the present application, are also hereby incorporated by reference in their entirety. Similarly the Danish patent application Ser. No. 2001 00218, filed Feb. 9, 2001, is hereby incorporated by reference in its entirety. All patent and nonpatent references cited in Danish patent application Ser. No. 2001 00218, are also hereby incorporated by reference in their entirety.

FIELD OF INVENTION

The present invention relates to transgenic scce mammals and mammalian embryos, their use as models of studying human diseases, to methods of using these models for identifying compounds and compositions effective for the treatment of these diseases, and to the compounds and compositions themselves. In particular, the invention relates to transgenic mammals overexpressing a scce gene in the skin. These model animals display a major change in phenotype characterized by a severe skin disorder and are useful for identifying compounds and compositions for the treatment of various human diseases.

GENERAL BACKGROUND

The skin as an organ is of interest from biological, medical, and cosmetological points of view. There are a large number of skin diseases that are either organ-specific, e.g. psoriasis and eczemas, or are manifestations of general disease, such as general allergic reactions. The fact that there are skin-specific diseases can be considered as a proof of the existence of molecular mechanisms that are unique for the skin. Analogously, studies on skin-specific molecular processes are of importance for the understanding and treatment of skin disorders. It seems reasonable to assume that several of these processes in one way or another are related to the most specialized function of the skin, that is the formation of a physico-chemical barrier between body exterior and interior. The physico-chemical skin barrier is localized in the outermost layer of the skin, the stratum corneum.

The stratum corneum is the most specialized structure of the skin. It is the end product of the differentiation process of the epidermis, that is the stratified squamous epithelium that accounts for the outermost portion of the skin. The majority of the cells of the epidermis consist of keratinocytes in various states of differentiation. The lowermost keratinocytes, the basal cells, reside on a basal membrane in contact with the dermis, that is the connective tissue of the skin, and are the only keratinocytes that have dividing capability. A fraction of the basal cells continuously leaves the basal membrane and goes through a differentiation process, which eventually makes the cells become building blocks of the stratum corneum. In this process the keratinocytes go through a number of adaptive changes. There is an increased content of cytoskeleton consisting of epidermis-specific cytokeratins. The intermediate filaments of contiguous cells are joined to a functional unit by an increased number of desmosomes. The most dramatic changes take place during the transition from the uppermost living cell layer, the stratum granulosum, to the non-viable stratum corneum in a process usually called keratinization. Covalently cross-linked proteins are deposited close to the inner aspect of the plasma membrane, forming a very resistant cell envelope. Furthermore a lipid-rich substance, originating in a keratinocyte-specific cell organelle, is secreted to the extracellular space and, by forming lipid lamellae, which surround the cells of the stratum corneum, constitutes the permeability barrier to hydrophilic substances. Finally all intracellular structures except the densely packed cytokeratin filaments disappear.

The cells of the stratum corneum, the corneocytes, are thus non-viable. This means that the regulation of various processes in the stratum corneum must be the result of a "programming" at a state where the keratinocytes are still viable. The turnover of the epidermis, which normally proceeds in about four weeks during which the cells are part of the stratum corneum for about two weeks, is ended by means of cell shedding from the skin surface in the process of desquamation. This process is an example of "programming" of the stratum corneum. A prerequisite for the function of the stratum corneum as a physico-chemical barrier is that its individual cells are held together by mechanically resistant structures, that is desmosomes. The degradation of desmosomes, which is a prerequisite for desquamation, must be regulated so as to give a cell shedding from the skin surface which balances de novo production of the stratum corneum without interfering with the barrier functions of the tissue.

Disorders of Keratinization

Under a large number of pathological conditions in the skin of varying severity, there are disturbances in the keratinization process. In psoriasis there is, in addition to a typical chronic inflammation, overproduction of an immature stratum corneum resulting in the typical scaling of this disease. There is a group of inherited skin diseases characterized by a thickened stratum corneum which leads to the formation of "fish scales", the so-called ichthyoses. In several of the ichthyoses there is a decreased rate of desquamation. Although less severe than the ichthyoses, "dry skin" (xeroderma) is also characterized by a stratum corneum from which corneocytes are shed, not as under normal conditions as single cells or as small aggregates of cells, but as large, macroscopically visible scales. This disorder is very common among elderly people and among atopics, that is individuals with a decreased resistance to skin irritants and a disposition to develop a characteristic form of endogenous eczema. In the acne diseases there is a disturbed keratinization in the ducts of the sebaceous glands, which leads to the formation of comedones and plugging. The formation of comedones precedes and is believed to provoke the inflammatory acne lesion.

Proteolytic Enzymes are Involved in Keratinzation

There are several stages in the keratinization process and during the turnover of the stratum corneum where proteolytic enzymes seem to play important roles. Certainly the disappearance of all intracellular structures except for the cytokeratin filaments occurring during the transition between viable and cornified epidermal layers must involve proteolysis. The transformation of profilaggrin to filaggrin, a protein that is believed to function in the special type of aggregation of cytokeratin filaments during keratinization, may be catalyzed by a specific proteinase. In the stratum corneum filaggrin is further degraded to low-molecular weight components which are probably important as "natural moisturizers". Furthermore there are proteolytic modifications of cytokeratin polypeptides during the keratinization process. Finally, proteolytic events are likely to play crucial roles in the degradation of intercellular cohesive structures in the stratum corneum in processes eventually leading to desquamation.

Stratum Corneum Cell Cohesion and Desquamation, the Role of Desmosomes

Intercellular cohesion in the stratum corneum as well as in the viable parts of the epidermis is mediated to a significant extent by desmosomes. A desmosome consists of two symmetrical halves, each of which is formed by two contiguous cells. Each desmosomal half has one intracellular part linked to the cytokeratin filaments and one part made up by glycoproteins anchored intracellulariy and with transmembranal and extracellular parts. The extracellular parts of these proteins, the desmogleins, are adhesion molecules, and through their interaction with each other in the extracellular space a cohesive structure is formed. The degradation of desmosomes seems to follow somewhat different routes in the stratum corneum of palms and soles as compared to non-palmo-plantar stratum corneum. In the latter tissue around 85% of the desmosomes disappear soon after the cells have become fully cornified. The remaining desmosomes, which are preferentially located at the villous edges of the extremely flattened celis, apparently remain intact up to the level where desquamation takes place. In palmo-plantar stratum corneum the corneocytes are much less flattened, and there is no extensive degradation of desmosomes in deeper layers of the tissue, in both tissues desquamation is associated with desmosomal degradation. In ichthyotic skin as well as in "dry skin", the number of desmosomes in the superficial layers of the stratum corneum has been shown to be increased.

Many of the tissue-specific molecular mechanisms of the skin are associated with the formation and turnover of the barrier-forming outermost layer of the epidermis, the stratum corneum, consisting of cornified epithelial cells surrounded by highly organized lipids. The stratum corneum is continuously being formed in the process of epidermal differentiation. In the efforts to understand the mechanisms by which a constant thickness of the stratum corneum is maintained via a continuos desquamation of surface cells, two human serine proteases, stratum corneum chymotryptic enzyme (SCCE) and stratum corneum tryptic enzyme (SCTE) have been identified (Hansson et al. 1994 and Brattsand et al. 1999). The cloning and expression of SCCE is described in WO95/00651, which hereby is incorporated by reference. Both enzymes belong to the kallikrein group of serine proteases, the genes of which are localized to a short stretch at chromosome 19q13.3–19q13.4 (Diamandis et al. 2000). SCCE is synonymous with human kallikrein 7 (KLK7). It should be noted however, that the numbering of kallikreins is not consistent between species. The expression of SCCE and SCTE seems to be restricted to squamous epithelia undergoing cornification and in which there is a need for desquamation (Ekholm et al. 2000).

Common inflammatory skin diseases may result in severe handicap by causing reduced function, stigmatization, and almost unbearable sensory symptoms. A dominating symptom of many of these diseases is itch, which in many instances may be extremely troublesome, causing severe disturbances in many aspects of every day life and sleeping patterns of sufferers. In atopic dermatitis, affecting more than 10% of children at some point of their childhood, pruritus is a major diagnostic criterion and always present in active disease. It has even been stated that "atopic dermatitis is an itch that when scratched erupts", and that "pruritus must be considered a quintessential feature of atopic dermatitis" (Beltrani, 1999). The mechanisms of itch are poorly understood, and available treatments are often unsatisfactory. This may be due, at least in part, to lack of satisfactory animal models (Greaves and Wall, 1996).

In inflammatory skin diseases such as psoriasis and atopic dermatitis evidence in favor of a central role for the immune system in pathogenesis is overwhelming. It seems likely that the development of the various disease-specific skin lesions and signs is the result of interactions at the cellular and molecular level between the immune system and skin-derived structures and molecules. In most studies aimed at understanding these interactions focus has been on cytokines, growth factors, and adhesion molecules. Although many of these components are produced by skin cells, they are not unique for the skin, but are more or less generally present in cells and tissues throughout the body. This fact may cause problems in e.g. development of skin-specific therapies. The situation would be different if one could find a truly skin-specific structure or molecule with a central role in the pathophysiology of inflammatory skin diseases. The present invention present new evidence that the serine protease stratum corneum chymotryptic enzyme (SCCE) may belong to this category of skin-specific molecules.

SUMMARY OF THE INVENTION

The present invention relates to results from studies aimed at elucidation of the possible involvement of one of these proteases, SCCE, in skin pathology. The human and murine scce-genes were characterized, and transgenic animals over-expressing human scce mRNA produced. The only gross phenotypic changes observed in these animals were found in the skin, which showed histological changes with several similarities to those seen in inflammatory skin diseases such as in the chronic stages of atopic dermatitis in humans. In addition, the transgenic animals showed signs of severe itch. Evidence of over-expression of SCCE in chronic lesions of atopic dermatitis in humans was also found corresponding to what has recently been shown in psoriasis (Ekholm et al. 1999). Taken together, the results give support for the idea that SCCE and related enzymes may be involved in the pathophysiology of itchy inflammatory skin diseases, and thus that SCCE may be a potential target for organ-specific treatment strategies. The transgenic animals of the invention may provide a new model for further studies of itch mechanisms and the testing of potential compounds and compositions for relieve of various skin diseases where itch is a component.

The human SCCE gene was isolated from a human leukocyte genomic library cat. no. HL 1111 j lot #3511 (Clontech, CA) by using cDNA probes derived from the human scce cDNA. Overlapping clones were isolated and the entire structural gene was sequenced by automated DNA sequencing and analyzed by ABI377 (Applied Biosystems, Foster City, Calif., USA). The entire sequence can be found using Gene Bank accession no AF 332583.

TABLE 1

Human SSE [org = Homo sapiens] Homo sapiens
stratum corneum chymotryptic enzyme gene
(SEQ ID NO:3).

TACCACATTTTCTTAATCCAGTCTATCACTGATGGACATTTAGGTTGATT

CCCTGTGTTTGCTGTGTCAATAGTTCTACAATGAACGTACGTGTCCATGT

GTCTTTAAACAGAATGATTTATATTCCTTTGGGTACACACACTGGGGCTT

ATGAGAGGGTGGAGAGTGGGAGGAAGGAGAGGATCAGAAAAAAATAACTA

ATGGGTACTAGGCTTAATACCTGGGTGATTAAATAATCTGTATAACAAAC

TABLE 1-continued

Human SSE [org = *Homo sapiens*] *Homo sapiens*
stratum corneum chymotryptic enzyme gene
(SEQ ID NO:3).

CCCCATGGCGCACGTTCACCTACGCAACAAACCTGCACATCCTGCACATG

TACCCCCGAACTGAAAAGTTAAAAAAAGAAAAATAAATATTTGCTTATAA

ATTAATAAATGAAGCCCTCAAAAATGTTCTATTAGATAATGTTAAGTACA

GACATTTTTGTTATAAATACATAATATACAAAGAAATCTATGTATAACAT

GATTAAAATGACCATAAGAACATAGATCCTAAACATGGCAAATATTAGTG

GGGTGGGGTTAGGGAAAGCGTTGTTTTTAACTTACACCTCTCTGTTAGAG

TTGGGAATGGGTTCAGGCGTAATTACAGGCACGACTGGGATCAGCTTGGA

CAAGTTCCCCCAGGCGGGCCAGAATTAGGATGTAGGGTCTAGGCCACCCC

TGAGAGGGGTGAGGGCAAGAAAATGGCCCCAGAAGCCGGGCGCAGTGGC

TCACGCCTGTAATCCCAGCACTTTGCGGGGCCGAGGCGGGCACATCATGA

GGTCAGGAGATCGAGACCATTCTGGCCAACATAGTGAAACCCGGTCTCTA

CTAAAAATACAAAAATTATCTGGGAGTGGTGGTGCGTGCCTGTAATCCCA

GGTACTCGGGAGGCTGAGGCAGGAGAATCACTTGAACCTGGGAGGCGGAG

CTGGCAGTGAGCCGAGATCGCGCCACCGCACTCCAGCCTGGCGATAGAGA

GAGACTCCATCCAAAAAAAGAAAGGAAGGGAGGGAGGGAGGAGGGAAGAA

AGAAAGAAAACCGCCCCAGAGAAGGACCCGAGCCAGAGCCTATTCTCTGA

GCTCAGCGACTGCTTGAATCCCGCTCCTGCCCCTCAGACCCAGCGCACCG

GGTCCCTCCCCCGAGAGCAGCCAGGAGGGACTGTGGGACCAGAATGTGCG

GGGGCGCAGGAGCTGGGCACCGCCCGTCCTTCGGAGGGAGGGTGGAGAGA

GAGTGCAGTGGTGCCAATTGCTCTCGCTGCGTCAGGGTTCCAGATAACCA

GAACCGCAAATGCAGGCGGGGGTGTCCCAGAGTCGGCTCCGCCTGCACCC

CAGGGCGCTGGGGCCGGGCATGGGCGGGGGGTGATATAAGAGGACGGCC

CAGCAGAGGGCTGAAGATTTTGGAGCCCAGCTGTGTGCCAGCCCAAGTCG

GAACTTGGATCACATCAGATCCTCTCGAGGTGAGAAGAGGCTTCATCAAG

GGTGCACCTGTAGGGGAGGGGGTGATGCTGGCTCCAGCCTGACTCTGCTC

TCGAGAGGTAGGGGCTGCAGCCTAGACTCCCGGTCCTGAGCAGTGAGGGC

CTGGAAGTCTGCAATTTGGGGCCTTTTAGGGAAAAACGAACTACAGAGTC

AGAAGTTTGGGTTCCACAGGGAAGGGCAAGATCGGAGCCTAGATTCCTGG

GTCTCTAGGGATCTGAAGAACAGGAATTTTGGGTCTGAGGGAGGAGGGC

TGGGGTTCTGGACTCCTGGGTCTGAGGGAGGAGGGCTGGGGCCTGGAC

TCCTGGGTCTGAGGGAGGAGGGGCTGGGGTCTCGACTCCTGGGTCTGAG

GGAGGAGGGCTGGGGCCTGGACTCCTGGGTCTGAGGGAGGAGGGCTG

GGACCTGGACTCCTAGGTCTGAGGGAGGAGGAGCTGGGCCTGGACTCCT

GGGTCTGAGGGAGGAGGGGCTGGGCCTGGACTCCTGGGTCTGAGGGAGG

ATGGGCTGAGGCCTAGACTCCTGGGTCTGAGGGAGGAGGGCTGGGGCCT

GGACTCCTGGGTCTGAGGGAGGAGGGGCTGGAGCCTGGACTCCTGGGCCT

GAGGGAGGAGGGGACTGAGACCTGGACTCCTAGGTCTGAGGGAGGAGGGAC

TABLE 1-continued

Human SSE [org = *Homo sapiens*] *Homo sapiens*
stratum corneum chymotryptic enzyme gene
(SEQ ID NO:3).

TGGGACCTGGACTCCTGGGTCTGAGGGAGGAGGAGCTGGGGGCCTGGACT

CCTGGGTCTGAGGGAGGCGGGGCTGGGGCCTGGACTCCTGGGTCTGAGG

GAGGAGGGGTTGGGGCCTGGACTCCTGAGCCTGAGGGAGGAGGGACTTGG

ACCTGGACTCCTAGGTCTGAGGGAGGAGGAGCTGGGGGCCTGGACTCCTA

GGTCTGAGGGAGGAGGGGCTGGGGGCCTGGACTCCTGGGTCTGAGGGAGG

AAGGTGCTAGGGTCTGGACTCTTGGGTATGAGGGAGGAGGAGGTTAGGGG

TCTGGACTTCTGAGTGTAAGGAAGGAGAGGCCAGAGAAAGGAATTTCTGG

GTCTGAGGGAGGAGGGGCTGGGGTTCTGGACCCCTAGGTCTGAGGGAGGA

GGGGCTGGGGCCTGGACTCCTGGGTCTGTGGGGGGAGGGGCTGGGGCCTG

GACCCCTGGGTCTGAGTGGGGAGGGCTGGGCCTGAATGCTTTCTCCTTCT

CAGCTCCAGCAGGAGAGGCCCTTCCTCGCCTGGCAGCCCCTGAGCGGCTC

AGCAGGGCACCATGGCAAGATCCCTTCTCCTGCCCCTGCAGATCCTACTG

CTATCCTTAGCCTTGGAAACTGCAGGAGAAGAAGGTGAAAGCTGGACTGG

GAAGTCTGACCTCACCTCAGGGCCCCACTGACCCTCTCCAAGGAGTCCC

TGAGTCAGAACCCTTCCCTCCTCAAACAGCTTCCATCCTGGGAGGACCAG

ACTGTCGGCTGAAGCCCCCGCTCTTCCTGCTTCTGCTGACTCAGGGGGTC

TCTGTCCCCTCCAGGCCCTGCCTCCTGTGCTCAGGGTCTCTCTGTGGTTC

CCCAGATGAGATGCGCCTCCTGGGTTCTGAGTGGGCTCCTTCTGTCTGT

CTCTATCCCTATCTCTTGCTTTCTCTGTATTTCTCCACACATTTTCATCT

GTCTCTGTCCATCTCTGACTCTGGGAATCCCTGAGGTGCAGCCTCAGCCT

TCCCCTAATGCTAGCTACCCACATGCTCCTCCATGTCTCCATCCAGCCCA

GGGTGACAAGATTATTGATGCGCCCCATGTGCAAGAGGCTCCCACCCAT

GGCAGGTGGCCCTGCTCAGTGGCAATCAGCTCCACTGCGGAGGCGTCCTG

GTCAATGAGCGCTGGGTGCTCACTGCCGCCCACTGCAAGATGAAGTAGGT

GCCACCCAAGTCTCTGCTGGAGGTGCGCCAGCATCTCCAGCTCGCTATGG

GGGTGGAAGGGCAGTCTTTCTGTGCCTACGGCTCTATTCTCCTCTCTCTG

GGTCTCTGTCCCCCTCTCTCTGGGCCTCTGTACCCCCTCTCCCTGGGGCT

CTGTCCCCTCTCTCCCTGGCTCTCTGTCTCCCTCTCTCTGGGTCTCTGT

CCCCCTCTCTCTGGATCTCTGTTCCCCTCTCTCTGTGTCTCTGTCCCCCA

TTCTCTCTAGGTCTCTGTTCCCCTCCTCTCTCTCTGGGTCTCTGTCCCT

CTCTCTCTGGTCTCTGTCCCCCTCTCTCTCTGGATCTCTGTCCCCCTCTC

CCTGGGCCTCTGTACCCCCTCTCCCTGGGGCTCTGTCCCCCCTCTCTGGG

TCTCTGTCTGCCTTTCTCTCTGGATCTCTGTTCCCCTCTGTGTCTCTGTC

CCCCTCTCTCTGGGTCTCTGTTCCCCTCCTCTCTTTCTGGGTCTCTG

TCCTCTCTCTGGGTCTCTGTCCCCCTCTCTCTGGTCTCTGTTCCCC

CTCCTCTCTCTGGGTCTCTGTCCCTCTCTCTCTGGGTCTCTGTCACCCT

CTCTCTCTGGGTCTCTGTCACCCTCTCTCTCTGGTCTCTGTTCCCCCTCC

TCTCTCTGTGGGTCTCTGTCCTCTCTCTCTGGGTCTCTGTCCCCTCTCTC

TABLE 1-continued

Human SSE [org = *Homo sapiens*] *Homo sapiens* stratum corneum chymotryptic enzyme gene (SEQ ID NO:3).

TCTGGTCTCTGTTCCCCCTCCTCTCTCTCCGGATCTCTGTCCCCCTCTCC
CTGGGGCTCTGTCCCCCTCTCTCCCTGGCTCTCTGTCTTCCTCTCTCTGG
GGCTCTGTCCCCCTCTCTCTGGTCTCTGTTCCCCTCTCTCTGGGTCTC
TGTCCCTCTCTCTGGGTCTCTGTCCCTCTCTCTGGATCTCTGTCCC
CCTCTCCCTGGGCCTCTGTACCCCCTCTCCCTGGGGCTCTGTCCCCCTCT
CTCTGGGTCTCTGTCTGCCTTTCTCTCTGGATCTCTGTTCCCCTCTGTGT
CTCTGTCCCCTCTCTCTGGGTCTCTGTTCCCCTCCTCTTTTCTGGG
TCTCTGTCCCTCTCTCTGGGTCTCTGTCCCCTCTCTCTGGTCTCT
GTTCCCCCTCCTCTCTCTGGTCTCTGTCCCTCTCTCTGGGTCTCTG
TCACCCTCTCTCTGGGTCTCTGTCACCCTCTCTCTGGTCTCTGTTC
CCCTCCTCTCTGTGGGTCTCTGTCCCTCTCTCTGGGTCTCTGTTC
CCCTCTCTCTGGTCTCTGTTCCCCCTCCTCTCTCTCCGGATCTCTGTC
CCCCTCTCCCTGGGGCTCTGTCCCCCTCTCTCCCTGGCTCTCTGTCTTCC
TCTCTCTGGGGCTCTGTCCCCCTCTCTCTGGTCTVTGTTCCCCTCTCT
CTGGGTCTCTGTCCCTCTCTCTGGGTCTCTGTCCCTCTCTCTCTGGAT
CTCTGTCCCCCTCTCTCTGGGTCTCTGTTCCCCTCTCTCTGGGTCTCT
GTCCCCTCTCCTCTCTGTGTCTCTCTCCCCCTCCTCTCTCTGTGTCTC
TGTCCCCCCTCCTATCTCTGTGTCTCTCTCCCCCCTCCTCTCTCTGGGTC
TCTGTCCCCCCCTCTCTGGGTCTCTGTCTCCCTCTCTCTGGGGCTCTGTC
CCCCTCTCTCTGGATCTCTGTTCCCCTCTCTCTGGGTCTCTGTCTCCC
CTCCTCTCTCTGTGTCTCTGTCCCCCCTCCTCTCTCTGGGTCTCTGTCCC
CACCCCGTCCCCAGGTCTTTGCACACCCTCTCTGTCACAGTGTCTCTTC
TGAATCTGTGAATGTCACTCCTCGCAGTGAGTACACCGTGCACCTGGGCA
GTGATACGCTGGGCGACAGGAGAGCTCAGAGGATCAAGGCCTCGAAGTCA
TTCCGCCACCCCGGCTACTCCACACAGACCCATGTTAATGACCTCATGCT
CGTGAAGCTCAATAGCCAGGCCAGGCTGTCATCCATGGTGAAGAAAGTCA
GGCTGCCCTCCCGCTGCGAACCCCCTGGAACCACCTGTACTGTCTCCGGC
TGGGGCACTACCACGAGCCCAGATGGTAGGTGGCCTCAGTGACCCAGGAG
TGCAGGCCCCAGCCCTCCTCCCTCAGACCCAGGAGTCCAGGCCCCCAGCC
CCTCCTCCCTCAGACCCAGGAGTCCAGGCCTCAGCCCCTCCTCCCTCAGA
CCCAGGAGTCCAGGCCCCAGCCCCTCCTCCCTCAGACCCGCGAGTCCAG
ACCCCAGCCCCTCCTCCCTCAGACCCAGCAGTCCTGGGCCCCAGACCCTC
CTCCCTCGGAACCAGGAGCCTGAACAACAGCCCTTCTGGTCCTCGCCCCC
ATCCTCTCTGACTGACAGCTCTCCCTGCTCCTCCCTGCAGTGACCTTTCC
CTCTGACCTCATGTGCGTGGATGTCAAGCTCATCTCCCCCCAGGACTGCA
CGAAGGTTTACAAGGACTTACTGGAAAATTCCATGCTGTGCGCTGGCATC
CCCGACTCCAAGAAAAACGCCTGCAATGTGAGACCCTCCCCCCCAATTCC

TCCCCAGTCCTGGGTACCCTGTCTGCATGCCCCAGGGACAGAGCTTGACC
CAAGTGACTGGGTACCAAGCCCGGCCTTGCCCTCCCCCCAGGCCTGGCCT
CCTCAGCTTTTTCCACCTCATTCTCTGCCTAGGTCAGGGGTGGGAGTTTA
CTTAGGGGCCGATGTGGCCCTGGGGATGGGACAGAGAGTTTAATAGGGGT
GAGAAAGTGGGGGTGGGACCAGGGAAGGAGACTGAGGTGCTGGCCTCAGG
CCCAAACCCTAAGGGGGCACCAAAAACCTCAGTGATTGAGATAAATCATA
ATGCAATATTTAAAAATAAAAATAAAAACTCATGCAGAAGTCCATGATGG
ACAAAATGTCACATTTTAAATAAAGAGCAGGTGGATCTTACTGAATTTTC
CCTTGCCGTAAGTACTAGCGTGGCTCAGCACAGCGCTGTACTGGCACTGT
CTTCATTTAAAATGTGGATACCATGCCCATCATGCAGTTTTATGTATTAC
ATTTGATTTCGTTAAGTACTGCATTGAAGTATTGTGTATTGCAGTTACTG
AGATTTTGTGCCTGAAGCTGATGACTCACTCACCTGACCCTGGCCCTGGT
TCCCGGGGAAAACACTCTTTCTCTCCACCTCCTCTCTGTTCCCTCTTTCT
GGCCTTTTGTCATCCCCTCTGTTTCTGAACAGTCTTCCCACATCTCTCTT
TGTGACATAATTTCATTTCATTCTTTTCCTCTTTGTTTTTTCTCTGTGTT
GAGCTAGCTTGCTCTCCCTCCCTTGTTCTCTCTCCATGCCCTCCTCTCTG
CTCTCTTTTCTCTGTGTTGAGCTAGCTTGCTCTCCCTCCCTTGTTCTCTC
TCCATGCCCTCCTCTCTGCTCTCTGTCTTCTCCCTCTTTCTCTTGCTTCT
CTCTCTCTCCTCCCCTCCCTCTCCTCTCCCTGCCCCCTGCTCTCTCT
TTTTTCCTCTCTCTCTGTCTCCTCTCTGGCCCTCTCCTCTTTCTCTCTCT
CCCCCACTTCTCTGTCTCTCTTCATCTCTCTCCCTCATCTCTCCTTGCCC
CCTCCTTTTACTGTCTCTCTCTTTCTCTTTCTTCTATCTCTCTCCTCTC
CCCGCCGCTCCCCATCTCTGTCTTTCTTTCTCTCTCTTTATTCTCCTCC
TCTCTTCCAGTCTCTCTCTCCTCTCCCCACCCCCACCCCATCTCTCTCCC
CACACCTTCCCCCCCTTTCTCTTTGTCTCTCTCTTCTACCTCTTTCTTCT
CCACCCCCATCTCTCTCTCTCTTCTCTTCCCACACCCTCCCCATCTCCCT
CATCTCTTTGTCTGTCTCTCTTCTCCCTCCTTCTTTTCCACCCCCATCTC
TCTGTCTCTCTCTCTCCCCATACCCTTTCCCTCTTCCTCATCTCTCTTTG
TCTCTCTCTCCTTTCCCTCTTTCTTCTCCACCTCCAACTCTCTCTGTCTC
TCCACACCCATCCTCCTTGCTCACATCTGCACCTTCAGCTGTCAGGGGAT
GTGGGATGGTGAGTGTTAGGGATAGAGGAGATGGGAGAGAGATGACTGTC
CTAGAGAATAGGGTGTTCCCCTTCTCCCCTGGTGAGGGCCAGTTTCATGA
ATGTGCAAGCTCTGCACGGACACAGAGCCCCACACTCAGAAGGGTCTCAA
ACTTAGTCTAATGCATTCCTGCTGTTGTCTTGAAATTCTCAATAATTTTT
GAACAAAGGGCCCTGCATTTTCGTTTTGCACCAAGTCCTGTAAATTATGT
AACTGGTCTTCACCCTGGTCTCCAGACCATCGTGTCCCCCTTTCCTGCG
CCACAGGGCACGCATCCACCCCTTGGAGATGATGTTCCTTCTCCCACTAG
CTTGGAGCAGGGTCCTTAACATTGGAAAATAAAGAGTGCTCTGATCCTGG

TABLE 1-continued

Human SSE [org = Homo sapiens] Homo sapiens stratum corneum chymotryptic enzyme gene (SEQ ID NO:3).

AAGCCCCACCCCTTCTCTGCAATTGGTCTCATTGGCCAAGGGTCAAACCA

GTGTCTTCAAAGGACCTAGTGTGTCCCTAGCACTAGCTCTCCCATTAGTC

CCCAGAGACAATGAGTCTCTTCTCATTGGCTATGGTGGAAGTCCATAATC

TGCAAGACAAAGACCGATAACTGAGGAATGTATGAGAATGAGTTGGGCTT

TGATCTGAAGCCAAAGTTAATCTCCGGCTCTATTCCCTCTAGGGTGACTC

AGGGGGACCGTTGGTGTGCAGAGGTACCCTGCAAGGTCTGGTGTCCTGGG

GAACTTTCCCTTGCGGCCAACCCAATGACCCAGGAGTCTACACTCAAGTG

TGCAAGTTCACCAAGTGGATAAATGACACCATGAAAAAGCATCGCTAACG

CCACACTGAGTTAATTAACTGTGTGCTTCCAACAGAAAATGCACAGGAGT

GAGGACGCCGATGACCTATGAAGTCAAATTTGACTTTACCTTTCCTCAAA

GATATATTTAAACCTCATGCCCTGTTGATAAACCAATCAAATTGGTAAAG

ACCTAAAACCAAAACAAATAAAGAAACACAAAACCCTCAGTGCTGGAGAA

GAGTCAGTGAGACCAGCACTCTCAAACACTGGAACTGGACGTTCGTACAG

TCTTTACGGAAGACACTTGGTCAACGTACACCGAGACCCTTATTCACCAC

CTTTGACCCAGTAACTCTAATCTTAGGAAGAACCTACTGAAACAAAAAAA

ATCCAAAATGTAGAACAAGACTTGAATTTACCATGATATTATTTATCACA

GAAATGAAGTGAAACCATCAAACATGTTCCAAAAGTACCAGATGGCTTAA

ATAATAGTCTGGCTTGGCACAACGATGTTTTTTTCTTTGAGACAGAGTC

TCTGTTGCTTGGGCTGCAATGCAGTGATGCAATCTTGGCTCACTGCAACC

TCCGCCTCCTGGGTTCAAGTGATTCTCGTGCTTCAGCCTCCCAAGTACCT

GGGACTACAGGTGTGCACCACCACACCAGGCTAATTTTTTGTGTATTTTT

ACTAGAGACAGGGTTTCACCATGTTGGCCAGCGTGGTCTTGAACGCCTGA

CCTCAGATGATCCACCCACCTTGGCCTCCCAAAGTGCTGGGATTACAGGC

ATGAGCCACCACGGCCAGCCCACAATGATATTACAAACCTATTAAAAATG

ATACTTAGACAGAATTGTCAGTATTATTCAAGAACATTTAGGCTATAGGA

TGTTAAATGACAAAAGGAAGGACAAAAATATATATGTATGTGACCCTACC

CATAAAAAATGAAATATTCACAGAATCAGATCTGAAAACACATGTCCCAG

ACTGCATACTGGGGTCGTCATGAGGTGTCTCCTTCCTTCTGTGTACTTTT

CCTTGAATGTGCACTTTTATAACATGAAAAATAAAGGTGGGAAAAAAGT

CTGAAGATCTAAGATTGGAGAGAGGTGACCTTTCAGGAAGGGAGACTAGA

AAGAAATATGTGCCTGGTTTTGAGCCCTGGTCCTGCCGGCCCTGTTCCAG

GGCATATTTCCATTTCCCAGATCTCAGTTTTTCCTGTCTGTAAAATGGGA

GAGAGAGGAAAGGATGGAGAGAGGAAGAAGGAAGGGAGGAGGGAGGAGAG

AACAGGCCAACTTCATCAGCGTGGGAAGGGGTGTGAAAGTGTTTCTGAGC

ATCTCACGAGTGACAAGTGAGGAGGGAGGCTGGCGGTTTTCAGAGGGATT

GGGATGACAGTAGACAGGACACAGGGGTCCCACAGGGGTCTGCCAGAAGT

AAGCAAACAGTGCCGGAGGAAGATGGTGGCACCTGCTCCCCAAGAAGGGA

GGGAAAGGAACCTCGGGAAGCGGGTAGGATGAGGGAGGAGTCCTCTGTGA

CTCAGAGCCTGGCCACAGCCCCAGCCATCTTAACATCAAAGATCCTCTGT

GTGGTCACACCTCAGACGCTGCTGACCGAGGAGCCACTCCAGCCCAGGAC

ACGCCCTCCTACCTGTTCTTCCTGTTTTTCTCCCAGAATTC

To isolate the murine scce gene cDNA probes derived from the murine scce cDNA (Bäkman et al. 1999) were used to screen and isolate clones from a 129SVJ Lambda Fix II genomic library cat. no. 946306 (Stratagene, La Jolla, Calif.). The entire gene sequence was determined and analyzed as described above. The entire sequence can be found using Gene Bank accession no, AF 339930 which is hereby incorporated by reference and is not shown here.

The amino acid sequences (as deduced from cDNA) of human and murine SCCE show around 80% similarity (Hansson et al. 1994 and Bäckman et al. 1999).

The genomic organization of the human and murine scce structural genes are schematically shown in FIG. 1. The most apparent difference between the structural genes from the two species is that the introns are longer in the human scce gene. As seen in FIG. 1 the scce genes from man and mouse both contain six exons, here indicated as black boxes, and have the translational start located in exon 2, and the stop codon in exon 6. Overall the organization of the exon-intron structures of the two genes is similar but due to shorter introns, the murine gene is smaller, approximately 4 kb as compared to 8 kb. In the human gene, the translation initiation site is found 60 nucleotides downstream the 5'-end of exon 2, and a potential TATA-box approximately 35 bp upstream of exon 1. Similarly, the murine initiation codon is positioned within the second exon, 39 nucleotides downstream of the intron-exon junction.

To generate transgenic mice with a modified regulation of expression compared to the endogenous scce, recombinant human scce gene under control of the SV40 early enhancer and promoter element was constructed as described in example 2. Three founders shown to be transgenic for SV40e-hscce integrated at a single site were obtained and lines were established by further breeding in C57BL/6JxCBA mice. As expected, initial characterization of the three lines revealed very large differences in levels of recombinant scce expression (see below). In line #1010, which has the highest hscce transcript levels, skin abnormalities were apparent, whereas in the two other lines no skin changes or other gross phenotypic deviations could be observed. For further detailed comparative studies of the #1010 transgenics one of the lines with apparently normal phenotype (#107) and non-transgenic littermates were included as controls.

The importance of the transcriptional regulation of the recombinant scce gene was demonstrated by the results achieved from other variants of transgenic mouse models. In these experiments different regulatory elements were inserted upstream of a genomic fragment comprising the human scce structural gene. For example, the mouse/human keratin 14 promoter (Vassar et al.) was utilized with the idea to target the expression of recombinant scce to more basal cell layers than is the normal distribution for endogenous SCCE. Also, a long genomic fragment containing the native human scce upstream regulatory sequence including the promoter was tested and evaluated. In these experiments the resulting transgenic mice neither showed any signs of altered neither skin morphology nor signs of itch. The detailed construct for recombinant scce expression comprising the sv40 early enhancer and promoter elements resulted in a surprisingly restricted distribution of expression and a transgenic mouse having very interesting changes in skin biology and clear signs of itch. This phenotype and expression pattern were surprising since the sv40 early regulatory sequences normally mediates high level transcription in proliferative cells whereas here the strongest expression in differentiated keratinocytes was observed.

To the knowledge of the present inventors, this is the first report of a mouse model for itchy inflammatory skin diseases produced by genetic manipulation of an enzyme, which may be skin specific. The SV40-scce transgenic mice are likely to give new insights into the pathophysiology of itchy human skin diseases and provide a new animal model for development of treatments directed at an organ-specific target. At the RNA-level expression of SCCE can be detected in several organs, although not at levels comparable to skin (Hansson et al. 1994 and Brattsand et al. 1999). In non-malignant tissues SCCE protein has so far been found only in high suprabasal cells in squamous epithella undergoing cornification and with a need for desquamation (Ekholm et al. 2000 and Ekholm et al 1998). The present inventors show here that over-expression of SCCE in mice at a site close to where it is normally expressed leads to a condition which to some extent simulates common, often debilitating human skin diseases such as atopic dermatitis and psoriasis.

In SV40-scce transgenic mice with phenotypic skin changes expression of transgenic SCCE, RNA as well as protein, was found also in other organs, especially small and large intestine, and lungs. The fact that no pathological changes were seen in these organs may be explained either by a resistance or unresponsiveness to effects mediated by SCCE, or by a lack of SCCE-activating enzymes in unaffected organs. SCCE, human as well as murine, is produced as an inactive precursor, which is converted to active protease by tryptic cleavage at a conserved site (Hansson et al. 1994 and Bäckmann et al. 1999). The enzyme responsible for SCCE-activation in the epidermis has not yet been identified.

The SV40-scce transgenic mice had a somewhat unexpected expression pattern of SCCE in the skin. Since the transgene construct contained the SV40 promoter it was expected to find the highest expression at sites with proliferating keratinocytes, i.e. in the basal layer of the epidermis and in hair follicles. On the contrary, no evidence of SCCE-expression was found in basal cells. Instead, as found by immunohistochemistry, there was expression in suprabasal cells, the intensity of which continuously increased with distance from the basal layer. This pattern is similar to that seen in psoriasis (Ekholm et al. 1999) lesions and chronic lesions in atopic dermatitis in humans. A possible explanation may be that the human scce-gene contains internal regulatory elements that suppress its expression in undifferentiated keratinocytes in the epidermis.

The mechanisms by which SCCE can cause a thickened epidermis with hyperkeratosis, a dermal inflammatory infiltrate, and itch remain to be elucidated. According to the current view the SCCE precursor is synthesized in high suprabasal epidermal keratinocytes and stored in lipid rich lamellar bodies. In the process in which a terminally differentiated keratinocyte is transformed from a viable cell to a corneocyte, i.e. a building block of the cornified surface layer of the epidermis—the stratum corneum—the contents of the lamellar bodies, including SCCE-precursor, are secreted to the extracellular space, where conversion of pro-SCCE to active protease is taking place (Sondell et al. 1995). One possibility is that SCCE, which has been activated as postulated, diffuses through the epidermis to the superficial parts of the dermis, thereby including epidermal thickening as well as dermal inflammation and activation of itch-mediating nerve endings. In previous studies on proteases as potential mediators of itch the enzymes were injected intradermally in human volunteers. Injection of trypsin and mast cell chymase caused itch by a mechanism believed to involve release by mast cells of histamine, whereas the itch caused by intradermally injected kallikrein appeared to be mediated by a mechanism not involving histamine (Hägermark et al. 1972 and Hägermark (1974). Treatment with an antihistaminic drug appeared not to relieve the itch seen in SV40-scce transgenic mice (A. Ny and T. Egelrud, unpublished observation). The fact that SCCE detected by immunohistochemistry in skin of SV40-scce transgenic mice was confined to superficial parts of the epidermis suggests that the dermal inflammation and the pruritus observed in these mice were not direct effects of active SCCE. In addition, signs of itch were not seen before the age of around 5 weeks, whereas overexpression of SCCE was found also in younger animals. An alternative explanation to the changes and signs caused by over-expression of SCCE in the epidermis could be that an increased proteolytic activity in the transition zone between viable epidermal layers and the stratum corneum may lead to release of mediators, which diffuse to other parts of the skin where they cause epidermal changes, dermal inflammation, and pruritus. A third possibility is that the epidermal hyperkeratosis and achantosis, dermal inflammation and pruritus are results of adaptive responses to a deterioration of the barrier function of the stratum corneum caused by increased proteolytic degradation of structures responsible for intercellular cell cohesion in the cornified layer. The proliferative response of the epidermis could be a result either of a direct effects of the released mediators on keratinocytes or an effect which is secondary to the dermal inflammation.

Recently a direct association between a defective epidermal barrier function and aberrant proteolysis in an inherited human condition with severe skin disease was described. Strong evidence was presented that the disease-causing mutations in Netherton's syndrome are localized to a gene coding for a precursor of serine protease inhibitors (Chavanas et al. 2000). These results, together with the present results, suggest that increased activity of serine proteases in the skin may indeed play a significant role in skin pathophysiology.

They also provide incentives for further exploring of possible new therapeutic principles for skin diseases.

DETAILED DISCLOSURE OF THE INVENTION

The present invention relates to a non human transgenic mammal or mammalian embryo having integrated within its genome a heterologous nucleotide sequence comprising at least a significant part of a nucleotide sequence coding for a stratum corneum chymotryptic enzyme (SCCE) or a variant thereof operably linked to a promoter that drives expression of the heterologous scce or a variant thereof in skin.

By the term "heterologous" is referred to a DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Preferably, the present invention relates to a transgenic mammal or mammalian embryo having integrated within its genome a heterologous nucleotide sequence comprising at least a significant part of a nucleotide sequence coding for a stratum corneum chymotryptic enzyme (SCCE) or a variant thereof operably linked to a promoter that drives expression of scce in epidermis.

By the term "a human stratum corneum chymotryptic enzyme (SCCE)" is meant a serine protease having the amino acid sequence SEQ ID NO:2 described in WO95/00651 and shown in the enclosed sequence listing. SCCE is synonymous with human kallikrein 7 (KLK7). However, the numbering of kallikreins is not consistent between species.

The bottom of the primary substrate specificity pouch (see Hansson et al., 1994) in SCCE from different species (residue no 170 in Table 2 above) contains a conserved asparagine residue, which is unique among known serine proteases. Also the sequence between this residue and the active serine residue (no. 176 in Table 2) is highly conserved. This suggests that the function, e.g. specialized catalytic properties, of SCCE is critically dependent on the mentioned asparagine residue.

TABLE 3

Alignment of partial deduced amino acid sequences from different species, corresponding to residues (-)7–27 of human SCCE (Hansson et al. 1994). In bold are shown the residues adjacent to activation site (C-terminal of Lys-(-1) of Arg (-1).

| | | |
|---|---|---|
| Cow SCCE | ...QEDQGNKSGEKIIDGVPCPRGSQPWQVALLKGSQLHCG... | (SEQ ID NO:9) |
| Pig SCCE | ...QEGQDKSGEKIIDGVPCPGGSRPWQVALLKGNQLHCG... | (SEQ ID NO:10) |
| Hum SCCE | ...EEAQGDKIIDGAPCARGSHPWQVALLSGNQLHCG... | (SEQ ID NO:11) |
| Rat SCCE | ...QGERIIDGYKCKEGSHPWQVALLKGDQLHCG... | (SEQ ID NO:12) |
| Mouse SCCE | ...QGERIIDGIKCKEGSHPWQVALLKGNQLHCG... | (SEQ ID NO:13) |

As discussed in example 6 the rat KLK7 in (Kroon et al. 1977) does not seem to be the rat SCCE. By the term "a SCCE variant" is meant a variant of said sequence not having exactly the amino acid sequence shown in SEQ ID NO:2, It may e.g. be a SCCE protease from another species, such as from a cow, pig, rat or mouse, or a synthetic polypeptide comprising a part of SEQ ID NO:2. The SCCE variant will generally react with antibodies raised against purified native or recombinant human SCCE and will generally have significant "SCCE activity", i.e. be a serine proteinase which can be inhibited by the same inhibitors as the spontaneous cell dissociation that can be induced in model systems with samples of cornified layer of skin incubated at neutral or near neutral pH at physiological temperature, i.e. about 37° C., as described in WO95/00651.

As can be seen from the following tables, there are significant similarities between SCCE from different species:

TABLE 2

Alignment of partial deduced amino acid sequences from different species, corresponding to residues 162–184 of human SCCE (Hansson et al. 1994) in bold are shown the residues ASC-170 and Ser-176

| | |
|---|---|
| Cow SCCE<br>NH2 ...AGIPNSRTNACNGDSGGPLMCKG... | (SEQ ID NO:4) |
| Pig SCCE<br>NH2 ...AGIPNSKTNACNGDSGGPLVCKG... | (SEQ ID NO:5) |
| Hum SCCE<br>NH2 ...AGIPDSKKNACNGDSGGPLVCRG... | (SEQ ID NO:6) |
| Rat SCCE<br>NH2 ...AGIPDSKTNTCNGDSGGPLVCND... | (SEQ ID NO:7) |
| Mouse SCCE<br>NH2    AGIPDSKTNTCNGDSGGPLVCND... | (SEQ ID NO:8) |

Active human SCCE is formed by cleavage C-terminal of K in the sequence KIIDG etc. This activation can be catalyzed by trypsin in vitro (Hansson et al., 1994). Examining the amino acid sequence adjacent to this cleavage site reveals a high degree of conservation between species. The consensus sequence is $G-X_1-X_2-I-I-D-G$ (SEQ ID NO:14), where $X_1$ is either aspartate (D) or glutamate (E), and $X_2$ is either lysine (K) or arginine (R). Aspartate and glutamate are functionally similar, both having negatively charged functional groups. The same holds true for lysine and arginine, which both have positively charged functional groups and forms sites for cleavage catalyzed by enzymes with trypsin-like primary substrate specificity. The consensus sequence adjacent to the activation site is unique among known serine proteases, suggesting an important function. It also suggests that there may exist enzymes in tissue (e.g.) epidermis, the specific function of which is SCCE-activation.

More specifically, the invention relates to a transgenic mammal or mammalian embryo having integrated within its genome a heterologous nucleotide sequence comprising at least a significant part of a nucleotide sequence coding for a protein with an amino acid sequence which has a sequence identity of at least 75% to the amino acid sequence shown in SEQ ID NO:2 and which contains the partial sequence glycine-$X_1$-$X_2$-isoleucine-isoleucine-aspartate-glycine (SEQ ID NO: 14), wherein $X_1$ is aspartate or glutamate and $X_2$ is lysine or argininine, operably linked to a promoter that drives expression in skin.

Preferably, the invention relates to a transgenic mammal or mammalian embryo having integrated within its genome a heterologous nucleotide sequence comprising at least a significant part of a nucleotide sequence coding for a protein with an amino acid sequence which has a sequence identity of at least 75% to the amino acid sequence shown in SEQ ID NO:2 and which contains the partial sequence (SEQ ID NO:15) $X_3$-asparagine-$X_4$-$X_5$-$X_6$ $X_7$-$X_8$-serine, wherein $X_3$ is any amino acid residue, $X_4$ is any amino acid residue, $X_5$ is a cystein residue $X_6$ is any amino acid., $X_7$ is a glycine residues $X_8$ is an aspartate residue, and the serine is the active serine residue characteristic of serine proteases, operably linked to a promoter that drives expression in skin.

In alternative embodiments, the encoded polypeptide has a sequence identity of at least 80% with the amino acid sequence shown in SEQ ID NO:2, such as at least 90%, e.g. at least 95%, preferably at least 98%, e.g. at least 99%.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

Alignment of two sequences for the determination of percent identity can be accomplished using a mathematical algorithm. A preferred, non-limiting example of a mathematical algorithm utilized for the comparison of two sequences is the algorithm of Karlin and Altschul (1990) Proc. Natl. Acad Sci. USA 87:2264–2268, modified as in Karlin and Altschul (1993) Proc. Natl. Acad. Sci. USA 90:5873–5877. Such an algorithm is incorporated into the NBLAST and XBLAST programs of Altschul, at al. (1990) 3. Mol. Biol. 215:403–410. BLAST nucleotide searches can be performed with the NBLAST program, score=100, wordlength=12, to obtain nucleotide sequences homologous to a nucleic acid molecules of the invention. BLAST protein searches can be performed with the XBLAST program, score=50, wordlength=3 to obtain amino acid sequences homologous to a protein molecule of the invention. To obtain gapped alignments for comparison purposes, Gapped BLAST can be utilized as described in Altschul et al. (1997) Nucleic Acids Res. 25:3389–402. Alternatively, PSI-Blast can be used to perform an iterated search which detects distant relationships between molecules. When utilizing the NBLAST, XBLAST, and Gapped BLAST programs, the default parameters of the respective programs can be used. See http.//www.ncbi.nim.nih.gov. Alternatively, sequence identity can be calculated after the sequences have been aligned e.g. by the program of Pearson W. R and D. J. Lipman (Proc Natl Acad Sci USA 85:2444–2448, 1998) in the EMBL database (www.ncbi:nim.gov/cgi-bin/BLAST). Generally, the default settings with respect to e.g. "scoring matrix" and "gap penalty" can be used for alignment.

The percent identity between two sequences can be determined using techniques similar to those described above, with or without allowing gaps. In calculating percent identity, only exact matches are counted.

By the term "at least a significant part of a nucleotide sequence coding for SCCE" is meant a nucleotide sequence (i.e. a DNA sequence or a RNA sequence) encoding a polypeptide having at least a part of the amino acid sequence shown in SEQ ID NO:2 and preferably resulting in an abnormal phenotype as described in the following. It is contemplated that it is useful and maybe even necessary to include intron sequences when preparing a nucleotide sequence coding for a SCCE or a variant thereof, i.e. one or more of the introns present in the human scce shown in Table 1 (see also annotations to GenBank accession number AF332583 which hereby is incorporated by reference) or one or more of the murine introns which may be deduced from the murine sequence. It is likely that not all of the intron sequences are necessary and that intron sequences from SCCE from other species or intron sequence from genes coding for other proteins may also be suitable and should be inserted in the nucleotide sequence coding for SCCE in a suitable manner.

It is contemplated that only a minor part of SCCE is necessary in order to obtain the abnormal phenotype. By the term "a significant part" is meant a nucleotide sequence encoding at least 50 amino acids of SEQ ID NO:2, e.g. at least 70 amino acids, at least 100 amino acids, at least 150 amino acids or at least 200 amino acids. These lengths are considered to be "a significant part of the peptide shown in SEQ ID NO:2". The polypeptides encoded may be longer than the above stated lengths, which will then indicate the parts which are common between the polypeptides encoded and SEQ ID NO:2. Generally, however, such nucleotide sequences will comprise the major part of the nucleotide sequence shown in SEQ ID NO:1 described in WO95/00651 and shown in the enclosed sequence listing, such as at least 500 nucleotides, e.g. at least 600 nucleotides, at least 650 nucleotides, at least 700 nucleotides, e.g. 750 nucleotides.

Such nucleotide sequences will generally hybridize with the complementary sequence to nucleotide sequence SEQ ID NO: 1 or a part thereof under stringent hybridization conditions. Within the concept of the present invention is thus a transgenic mammal or mammalian embryo having integrated within its genome a nucleotide sequence which hybridizes with the complementary sequence to the nucleotide sequence SEQ ID NO: 1 or a part thereof under stringent hybridization conditions, preferably under highly stringent conditions, said sequence comprising at least a significant part of a nucleotide sequence coding for a stratum corneum chymotryptic enzyme (SCCE) or a variant thereof operably linked to a promoter that drives expression of scce in skin. In a particularly interesting embodiment of said transgenic mammal or mammalian embryo said promoter drives expression of scce in epidermis. The term "stringent" when used in conjunction with hybridization conditions is as defined in the art, i.e. 15–20° C. under the melting point $T_m$, cf. Sambrook et al, 1989, pages 11.45–11.49. Preferably, the conditions are "highly stringent", i.e. 5–10° C. under the melting point $T_m$. However, due to the degeneracy of the genetic code also nucleotide sequences, which have only minor resemblance to SEQ ID NO:1, may be able to encode a SCCE.

The vectors for expressing the nucleic acids having nucleotide sequences coding for a SCCE require that the nucleic acid having a nucleotide sequence coding for a human SCCE be "operatively linked." A nucleic acid is operatively linked when it is placed into a functional relationship with another nucleic acid sequence. For instance, a promoter or enhancer is operatively linked to a coding sequence if it affects the transcription of the sequences. The promoter and enhancer may be the same or two different entities. The SV40 early promoter is an example of an integrated promoter and enhancer. Operatively linked means that the DNA sequences being linked are contiguous and, where necessary to join two protein-coding regions, contiguous and in reading-frame. By the term "a SCCE construct" is meant a nucleotide sequence comprising at least a significant part of a nucleotide sequence coding for a stratum corneum chymotryptic enzyme (SCCE) or a variant thereof operably linked to a promoter that drives expression of scce in skin or part of the skin. In particular a SCCE construct that comprise a promoter that drives expression of scce in epidermis is contemplated.

In a preferred embodiment according to the present invention, the promoter is a ubiquitous promoter. By the term "ubiquitous promoter" is meant a promoter that is active in many different cell types of the host organism in contrast to a promoter whose expression is specific for one or a few target cell types (a tissue-specific promoter). An example of "ubiquitous" promoter is the SV40 promoter and variations thereof such as the SV40-early promoter. Other examples of ubiquitous promoters are other viral promoters such as polyoma early promoter, retroviral long terminal repeats (5'-LTR) adenovirus promoters, and house keeping cellular genes such as β-actin, and ribosomal protein promoters. The promoter is preferably a heterologous promoter. It is contemplated that constitutive viral promoters, such as polyoma early viral promoter, Ebstein Barr virus promoter and retroviral long term repeat LTR promoters will be useful in the construction of transgenic mammals according to the invention.

An important embodiment of the invention relates to a transgenic mammal or mammalian embryo selected from the group consisting of rodents, such as mice, rats and rabbits, cats and dogs. A preferred embodiment of the invention is a transgenic mammal or mammalian embryo, which is selected from the group consisting of mice.

Preferably, the transgenic mammal or mammalian embryo according to the invention comprises a heterologous nucleotide sequence comprising a significant part of DNA sequence coding for human SCCE as shown in SEQ ID NO:1. The transgenic mammal or mammalian embryo according to the invention preferably comprises a nucleotide sequence coding for a significant part of the peptide shown in SEQ ID NO. 2 as defined above. In preferred embodiments, the DNA sequence codes for the peptide corresponding to amino acid no. −7 through no. 224 of human SCCE (with the first AA of active human SCCE numbered "1"), which corresponds to AAs 23–253 of the amino acid sequence shown in SEQ ID NO. 2; the peptide corresponding to amino acid no. 1 through no. 224 of human SCCE, which correspond to AAs 30–253 of the amino acid sequence shown in SEQ ID NO. 2; or the peptide shown in SEQ ID NO. 2. Presently preferred embodiments relate to transgenic mammals or mammalian embryos according to the invention, wherein the DNA sequence comprises the DNA shown in SEQ ID NO. 1 or the DNA sequence is SEQ ID NO:1.

In an important embodiment of the invention, the transgenic mammal or mammalian embryo according to the invention exhibits an abnormal phenotype, such as an abnormal skin phenotype and/or a predisposition for cancer, e.g. a predisposition for ovarian cancer.

Preferably, the mammal or mammalian embryo according to the invention exhibits an abnormal skin phenotype resembling one or more inflammatory skin diseases characterized by epidermal hyperkeratosis, acanthosis, epidermal and/or dermal inflammation and/or pruritus, e.g. inherited skin diseases with epidermal hyperkeratos, ichthyosis vulgaris, psoriasis, chronic atopic dermatitis or chronic eczema. The mammal or mammalian embryo according to the invention may thus exhibit epidermal hyperkeratos, achantosis, epidermal/dermal inflammation and/or pruritus.

The invention further relates to a method for making a transgenic non human mammal or mammalian embryo having integrated within its genome a heterologous nucleotide construct comprising at least a significant part of a nucleotide sequence coding for a stratum corneum chymotryptic enzyme (SCCE) or a variant thereof operably linked to a promoter that drives expression of scce or a variant thereof in skin, the method comprising (a) constructing and amplifying a nucleotide sequence comprising at least a significant part of a nucleotide sequence coding for a stratum corneum chymotryptic enzyme (SCCE) or a variant thereof operably linked to a promoter that drives expression of scce or a variant thereof in skin, (b) introducing into a non-human cell said heterologous nucleotide construct, (c) using said cell or the progeny of said cell to create a number of putative transgenic non-human mammals or mammalian embryos, (d) selecting said non-human mammal or mammalian embryo having said heterologous nucleotide construct integrated within its genome.

In one embodiment of the invention said transgenic mammal or mammalian embryo have integrated a nucleotide sequence coding for human SCCE or a variant thereof as defined above operably linked to a promoter that drives expression of scce in epidermis. In a preferred embodiment, the invention relates to a method for making a transgenic mammal according to the invention, where the mammal exhibits an abnormal phenotype as defined above. The method comprises introducing the SCCE-construct into an ovum or embryo of the mammal by physical, chemical or viral means, e.g. by electroporation, transfection, microinjection or viral infection. In a preferred embodiment of the invention, the SCCE-construct is microinjected into an ovum or embryo of the mammal or into embryonal stem cells of the mammal. In a preferred embodiment the method according to the invention comprises microinjecting the SCCE-construct into C57BL/6JxCBA-f2 mice ovum or embryos. The method preferably further comprises breeding the resulting mice with C57BL/6JxCBA or with C57BL/6J to obtain transgenic litter and stable mouse lines. Such stable cell lines derived from the transgenic mammals comprising a SCCE construct as described above are contemplated to be useful for e.g. high throughput screening of suitable compounds as described in the following.

Another aspect of the invention relates to the use of the transgenic mammal or mammalian embryo according to the invention as a model for the study of disease with the aim of improving treatment, relieve or ameliorate a pathogenic condition, for development or testing of a cosmetic or a pharmaceutical formulation or for the development of a diagnostic method. A preferred use according to the invention of said transgenic mammal or mammalian embryo is as a model for a skin disease or a model for cancer such as ovarian cancer.

An important aspect of the invention relates to a method of screening for a compound or composition effective for the prevention or treatment of an abnormal or unwanted phenotype, the method comprising (a) administering a compound or composition to a transgenic mammal having integrated within its genome a nucleotide sequence coding for at least a significant part of SCCE operably linked to a promoter that drives expression of the scce in an organ, wherein the rodent exhibits an abnormal phenotype, (b) evaluating the appearance of the relevant organ and/or the behavior of a mammal treated according to step (a), and (c) comparing the appearance of the relevant organ and/or the behavior of a treated rodent with an untreated control mammal.

An important aspect of the invention relates to a method of identifying a compound or composition effective for the prevention or treatment of an abnormal or unwanted phenotype, the method comprising (a) administering a compound or composition to a transgenic mammal having integrated within its genome a nucleotide sequence coding for at least a significant part of SCCE operably linked to a promoter that drives expression of the scce in an organ, wherein the rodent exhibits an abnormal phenotype, (b) evaluating the appearance of the relevant organ and/or the behavior of a mammal treated according to step (a), and (c) comparing the appearance of the relevant organ and/or the behavior of a treated rodent with an untreated control mammal.

(d) identifying the compound or composition as being effective for the prevention or treatment of the abnormal or unwanted phenotype.

In preferred embodiments, the organ is the ovaries or the skin, or more preferably the epidermis. A presently preferred embodiment of the invention relates to a method of screening for or identifying a compound or composition effective for the prevention or treatment of itchy inflammatory skin diseases such as ichthyosis vulgaris, prurigo nodularis, neurodermatitis, lichen planus. Other preferred embodiments of the invention relate to a method of screening for or identifying a compound or composition effective for the prevention or treatment of chronic atopic dermatitis and psoriasis. Also, the invention relates to a method according to the invention for screening of a cosmetic composition.

Another important aspect of the invention relates to a method of preparing a pharmaceutical composition which comprises i) identifying a compound or composition as being effective for the prevention or treatment of an abnormal or unwanted phenotype using a method according the present invention, and ii) mixing the compound with a pharmaceutically acceptable excipient or diluent.

In particular, the invention relates to a cosmetic or pharmaceutical composition that has been discovered or developed by use of the above methods comprising use of a transgenic mammal or mammalian embryo as described above. In this respect the invention relates to pharmaceutical formulations for systemic treatment as well as for cosmetic and pharmaceutical formulations for topical application on the skin or epithelium.

Yet a further aspect of the invention relates to a method of treating or preventing an abnormal or unwanted phenotype which method comprises administering to a patient suffering from such an abnormal or unwanted phenotype a pharmaceutical composition prepared according to a method of the present invention.

A preferred embodiment of the invention relates to a method of treating or preventing itchy inflammatory skin diseases such as ichthyosis vulgaris, prurigo nodularis, neurodermatitis, lichen planus. Other preferred embodiments of the invention relate to methods of treating or preventing chronic atopic dermatitis and psoriasis.

LEGEND TO FIGURES

FIG. 1.

Organization of the human and murine structural genes and the recombinant sv40e/hscce gene. The six exons are indicated as black boxes. The translational start sites, located in exon 2, are indicated with "ATG", and the stop codons in exon 6 with "TAA". Also the position of the sv40e transcriptional regulatory element in the construct used to generate the transgenic animal is indicated by an arrow.

Figure 2:
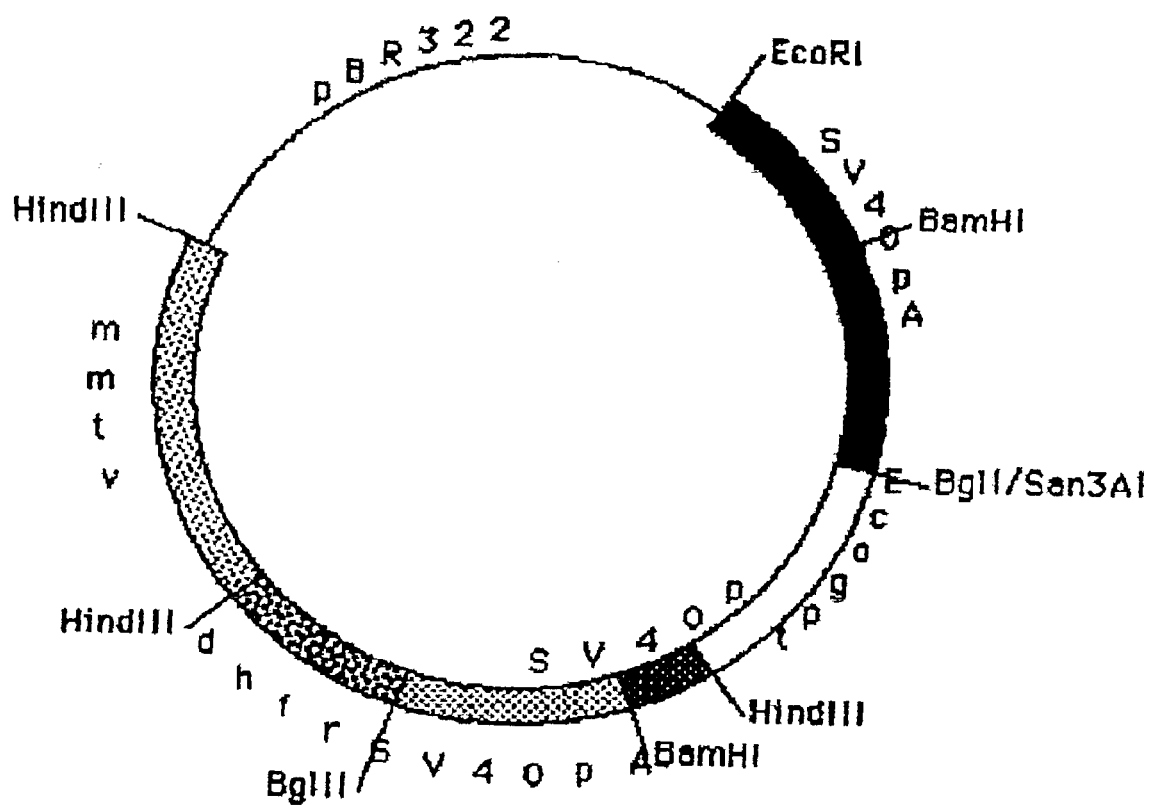

FIG. 2
pS99.

FIG. 3.

Figure 3:
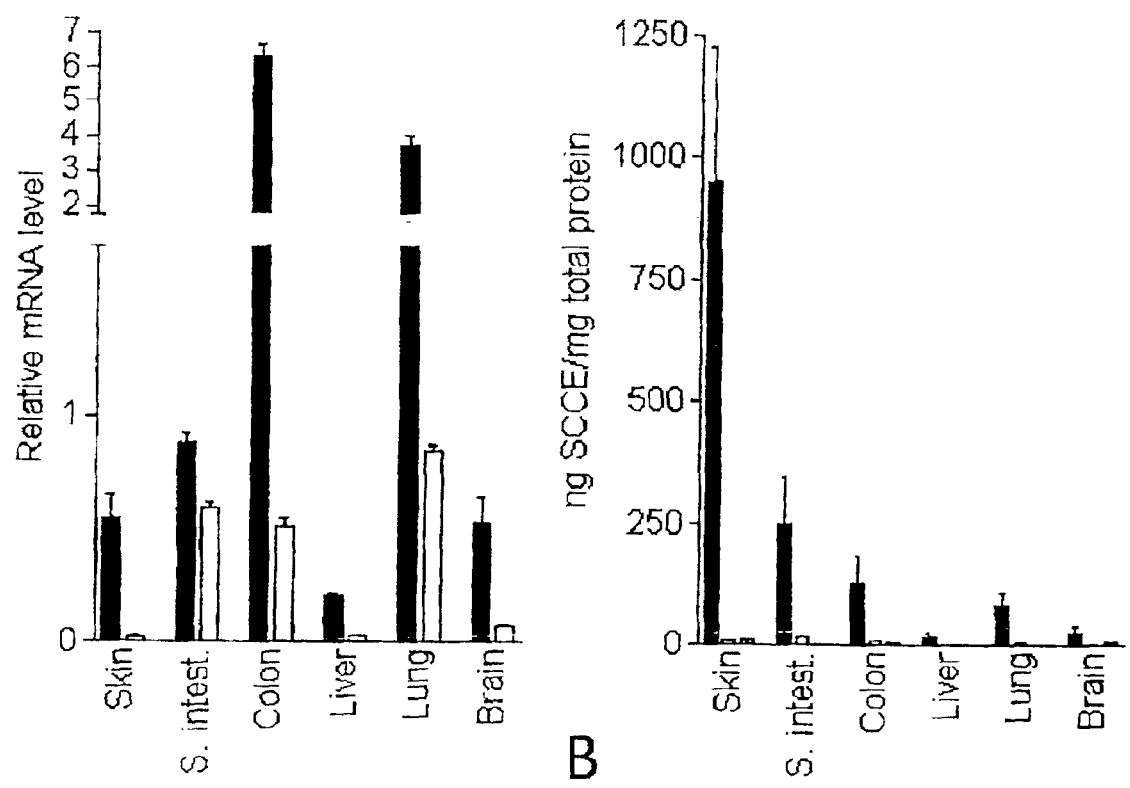

FIG. 3A: Real time quantitative PCR analyses of recombinant human scce mRNA in various tissue preparations from the transgenic lines #1010 (black bars) and #107 (empty bars). Analyses in triplicate were carried out on RNA samples comprising pooled material from three animals from each line. The murine acidic ribosomal phosphoprotein P0 was used as internal standard. Mean and SD.

FIG. 3B ELISA-analyses of SCCE-protein in various tissues from the transgenic lines #1010 (black bars) and #107 (empty bars), and non-transgenic siblings (gray bars). Analyses in triplicate were carried out on pooled extracts from three animals from each line and controls. Mean and SD.

FIG. 4

Pro-SCCE and active SCCE in skin from #1010 scce-transgenic mice. Hu=extract of human plantar stratum corneum; Tg=extract of skin from #1010 transgene; Wt=extract of skin from wild type littermate. Approximately 0.1 g of mouse skin was homogenized in 10 ml of 1 M acetic acid and extracted over night at 4° C. After clearing by centrifugation extracts were aliquoted, lyophilized, and resolubilized in electrophoresis sample buffer.

Figure 4:
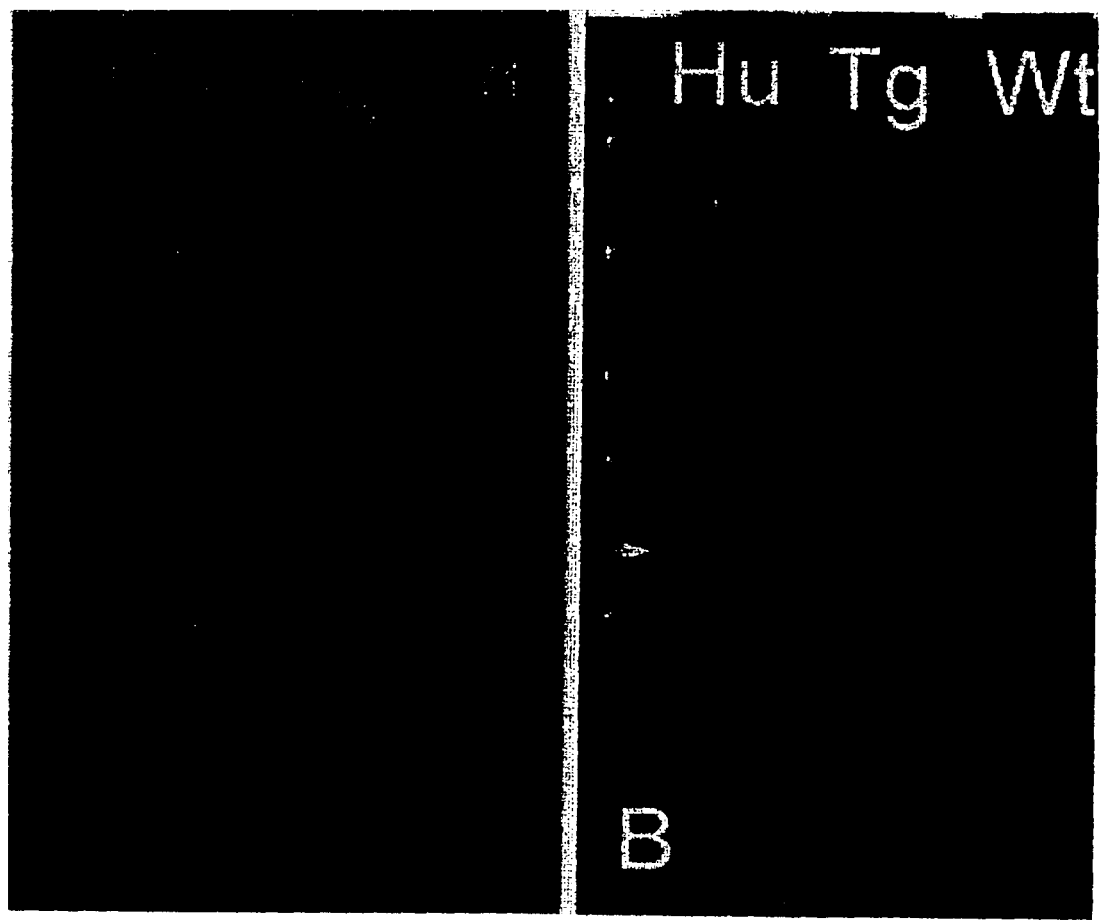

FIG. 4A: Immunoblot with SCCE-specific antibodies, reduced samples. Arrowheads denote, from top to bottom, glycosylated pro-SCCE, mixture of unglycosylated pro-SCCE and glycosylated SCCE, and unglycosylated SCCE. Amount of sample applied corresponding to 0.1 mg and 4.5 mg of skin for Tg and Wt, respectively.

FIG. 4B: Zymography in 12.5% acrylamide gel with 1% casein; non-reduced samples. Amount of sample applied corresponding to 0.4 mg and 4.5 mg of skin for Tg and Wt, respectively. Arrow denotes SCCE.

To the far left (marked by asterisks) molecular weight markers; from top 106, 81, 47.5, 35.3, 28.2, and 20.8 kDa respectively

FIG. 5.

Scratching behavior of scce-transgenic (#1010) mice. Twenty one mice, (11 transgenes, 5 females; 10 wild type litter mates, 2 females) were observed every fifth day for 45 days, starting when the mice were 5–6 weeks of age. At each observation point mice were transferred to individual cages, and episodes of scratching with hind or front paws were counted during three 5-min periods with 2.5 min lapsing from the transfer to the cage to the first counting, and between counting periods. The results for the three observation periods were pooled and the number of episodes of scratching per min calculated. In A the number of episodes of scratching (mean and SEM for all animals in each group) is shown, in B the percentage of animals with at least one episode of scratching per min is given. ■ (square)=#1010 transgenic mice; ▲ (triangle)=wild type litter mates.

FIG. 6.

Histology and SCCE-immunohistology of skin from scce #1010 transgenic mouse and control; comparison with normal human skin and chronic lesion of atopic dermatitis. Formaldehyde fixed and paraffin embedded samples. A–B stained with hematoxylin and eosin. C–F immunoperoxidase staining with SCCE-specific antibodies, contra-staining with hematoxylin. A and C: #1010 transgenic mice, 5 weeks of age. B and D: non-transgenic littermate. E: Atopic dermatitis. F: Normal human skin. Bar=50 μm.

FIG. 7.

The effect on itch in scce-transgenic mice of the glucocorticoid triamcinolone acetonide. Squares=triamcinolone acetonide, n=4; triangles=controls (saline), n=6. *=statistically significant difference (p<0.05) between controls and treated group.

FIG. 8.

The effect on itch in scce-transgenic mice of the antihistamine loratidine. Black bars=loratidine (n=7); White bars=controls (n=7); mean and SE. There were no statistically significant differences in frequency of scratching between treatment group and control group.

EXAMPLES

The following examples are provided for illustration and are not intended to limit the invention to the specific examples provided.

Example 1
Isolation and Cloning of the Human SCCE Gene.

The human SCCE gene was isolated from a human leukocyte genomic library cat. no. HL 1111 j lot # 3511 (Clontech, CA) by using cDNA probes derived from the human scce cDNA. A 253 bp cDNA fragment was amplified from pS500 (Hansson et al., 1994) by PCR using SYM3300 (5'-GGTGGCCCTGCTAGTGGCA-3') (SEQ ID NO: 16) and SYM3301 (5'-CACCATGGATGACACAGCCTGG-3') (SEQ ID NO: 17), $^{32}$P-labelled by random priming using oligo-labelling kit (Amersham, UK) and used as a probe for screening. The fragment covers bases 149 to 401 of the published human SCCE cDNA sequence (Hansson et al., 1994). Approximately 5×10$^5$ plaques were screened. Filters were prepared, prehybridized and hybridized at 65° C., and washed at 65° C. and 25° C. In accordance with the membrane manufacturers recommendations (Colony/Plaque Screen™ hybridization transfer membranes DuPont NEN, MA). Filters were exposed to Hyperfilm-MP (Amersham, UK). After three rounds of screening, individual positive clones were selected, and phage DNA was isolated using standard techniques (Sambrook et al., 1989). Phage DNA was digested with several restriction enzymes and Southern blotting was performed using three different probes. First, the 253 bp 5'-fragment described above was used. Second, a 618 bp 3'-noncoding cDNA fragment was used as a probe. The fragment was amplified by PCR using pS501 as template, forward primer SYM3302 (5'-AATAAAGAAACACAAAACCC-3') (SEQ ID NO: 18) and reverse primer SYM3418 (5'-TGTAATATCATTGTGGGC-3') (SEQ ID NO: 19). pS501 is a plasmid containing 1888 bp human SCCE cDNA isolated from a λgt11 keratinocyte cDNA library ligated into EcoRI site of pUC19 and covers cDNA with coding sequence from amino acid four over the stop codon and contains 868 bp extra untranslated 3' sequence. Finally, a 897 bp fragment containing the entire coding SCCE cDNA sequence was isolated from EcoRI/DraI digested pS500 (Hansson et al., 1994) and used as a probe. Probes were labelled and hybridization was performed as described above. Two positive clones were digested with SalI and cloned into pUC19 generating pS772 and pS773. In order to determine the DNA sequence of the human SCCE gene, several overlapping subclones of pS772 and pS773 were generated in pUC19. Subclones were sequenced using the dideoxy chain termination method (T7 sequencing kit, Pharmacia, Sweden or the Dye Terminator Cycle Sequencing Ready Reaction kit, PE Applied Biosystems, CA) with M13 forward and reverse primers as well as specific primers.

Isolation and Cloning of the Mouse SCCE Gene.

To isolate the mutine SCCE gene, a 430 bp cDNA fragment was isolated from HindIII/SalI digested pS506 (Bäckman et al., 1999). The fragment was $^{32}$P-labelled by random priming using oligo-labelling kit (Amersham, UK), and used as probe to screen a 129SVJ Lambda Fix II genomic library (Stratagen, CA). Approximately 1×10$^6$ plaques were screened. The blots were prepared, prehybridized and hybridized at 65° C. as described by the manufacturer (Colony/Plaque Screen™ hybridization transfer membranes DuPont NEN, MA). Washing was also performed as described in the hybridization protocol and membranes were exposed to Hyperfilm-MP (Amersham, UK). Individual positive clones were selected after three rounds of screening. A few positive plaques were further investigated by PCR using SYM4118 (5'-GGATGTGAAGCTCATCTC-3') (SEQ ID NO: 20) and SYM4121 (5'-TGGAGTCGGGATGCCAG-3') (SEQ ID NO: 21). Obtained PCR products were analyzed by Southern blotting using the probe and conditions described above. Phage DNA was isolated from confirmed positive clones using standard techniques. Southern analysis was performed on phage DNA digested with a panel of restriction enzymes using the probe and conditions described above. One of the positive clone was digested with SacI, and a fragment of ~15.5 kb was isolated and cloned into pUC19 generating pS714. Several overlapping subclones of pS714 were generated in pUC19. DNA sequencing of the subclones were performed as described for the human SCCE gene.

Primer Extension Analysis.

Two exon 1-specific oligonucleotides; one human and one mouse, were used to determine the 5'-prime ends of the human and murine SCCE transcripts. To determine the start of the human transcript (Ausubel et al.) a PCR fragment of 346 bp was amplified from plasmid p5779 (A subclone covering 5'-untranslated sequence, exons 1–3, 5'-end of exon 4 and introns 1–3) using forward primer SYM4720 (5-GGGAGGGTGGAGAGAGA GTGCAGTG) (SEQ ID NO: 22) and reversed primer SYM4899(5'-AGTCTAGGCTGCAG CCCCTAC-3') (SEQ ID NO: 23). To prepare a 245 bp $^{32}$P-dCTP labelled single stranded probe, primer hEXON1 (5'-CTCGAGGGATCTGATGTGATCC-3') (SEQ ID NO: 24) was annealed to the amplified fragment and labelling was performed using the Prime-A-Probe TM DNA labelling kit (Ambion, Austin, Tex., USA). 10$^6$ cpm labelled probe was mixed with 50 μg total RNA from human skin. Hybridisation and S1 treatment was performed using S1-Assay™ (Ambion, Austin, Tex., USA). The final product was analyzed on a sequencing gel. Dideoxy sequencing reactions of pS779 primed with oligo hEXON1 were used as size markers.

The start of the murine transcript was determined using SacI linearized pS721 (A subclone covering 5'-untranslated sequence, exons 1–3, introns 1–2 and 5'-end of intron 3). A 225 bp $^{32}$P-dCTP labelled single stranded probe was prepared by annealing of primer mEXON1 (5'-CTGGGAGTGACTTGGCGTGGCTCT-3') (SEQ ID NO; 25) to the linear plasmid and labelling was performed using the Prime-A-Probe TM DNA labelling kit (Ambion, Austin, Tex., USA). 106 cpm labelled probe was mixed with 50 μg total RNA isolated from mouse tail. Hybridization and S1 treatment was performed using 51-Assay™ (Ambion, Austin, Tex., USA). The obtained product was analyzed as described above using sequencing reactions of pS721 primed with oligo mEXON1 as size markers.

Results (Nucleotide Sequences in Gene Bank: Human scce (hSCCE): Accession Number AF332583; Murine scce (mSCCE): Acession Number AF339930.)

A human leukocyte EMBL3λ genomic library was screened using a probe made from the coding region of human sscce cDNA (Hansson et al., 1994) individual positive clones were identified. Based on restriction analysis and Southern blotting two overlapping clones, 12 and 15.5 kbp in size respectively, were selected. These clones were spanning the entire scce cDNA. The genomic structure of the human scce structural gene comprises six exons and spans approximately 8 kb. The organization and sizes of exons and introns are shown in FIG. 1. The translation initiation site (designated +1) is found 60 nucleotides downstream the 5'-end of exon 2.

To isolate the murine scce gene, a SVJ129 genomic λFIX™ II library was screened using a probe corresponding to the coding region of murine scce cDNA (Bäckman et al.).

Among the isolated clones one harboring about 15.5 kb was shown to contain the entire murine structural gene. A major part comprising 11770 nucleotides was sequenced and the murine structural scce gene was shown to be shorter than the human gene. However, the overall organization reveals several similarities with the human homologue and also consists of six exons (FIG. 1). Since the polyadenylation site of the murine cDNA has not been identified so far, the exact size of exon 6 could not be determined. However, a putative poly A site was localized 136 bp 3'-prime of the stop codon. The translation initiation site (designated+1) is found in exon 2, 39 nucleotides 3' of the intron 1 3'-intron-exon junction.

To determine the 5' ends of the human and murine transcripts primer extension studies were performed. Sequence analysis of the human cDNA (exon1, unpublished results) revealed that the major human primer extension product extends to the nucleotide identified at the 5' end of the human cDNA sequence (Hansson et al). Analysis of the two major products obtained from the murine gene by primer extension reveal two different transcription starts. One product extends to one nucleotide 5' of the murine SCCE cDNA 5' end (Bäckman et al.). The other product extends to one nucleotide 3' of the cDNA 5' end.

Example 2

Generation and Gross Phenotypic Characterization of of scce Transgenic Mice with the hscce Gene Under Control of the SV40e Promoter Construction of Transgene.

In order to overexpress the human genomic scce structural gene under transcriptional regulation of the simian virus 40 early, SV40e, enhancer and promoter, an expression vector was constructed. The scce genomic DNA was modified by insertion of HindIII linkers 20 bp upstream of the start codon and 4.8 kb downstream of the stop cod on, respectively. The resulting HindIII scce fragment was the ligated to a 325 bp BamHI/HindIII fragment of pS99 (FIG. 2) containing the SV40e enhancer and promoter elements and cloned into pBluescript SK+/− (Stratagene) resulting in pAM119. For gene transfer, the plasmid pAM119 was digested with BamHI and ClaI and the SV40e/scce fragment of about 10.7 kb was isolated and purified by electroelution before microinjection into one-cell stage mouse ova.

Transgenic mice were generated in C57BL/6JxCBA-f2 embryos by standard microinjection procedures (Hogan et al, 1986). The 10.7 kb SV40e/scce fragment to be injected was excised from the pAM119 plasmid by restriction enzyme cleavage with BamHI and ClaI, separated by gel electrophoresis through an agarose gel, cut out, isolated using isotachophresis and precipitated with ethanol.

Identifying Transgenic Animals.

To identify transgenic animals, DNA was extracted from tall biopsies of 3-wk old mice and the DNA was analyzed either by Southern blot analyses or with PCR as described in Ausubel et al. The PCR analysis was performed using primers specific for human scce (IE2: 5'-GCT CTC CCA TTA GTC CCC AGA GA-3' (SEQ ID NO: 26), MJ2: 5'-CCA CTT GGT GAA CTT GCA CAC TTG-3' (SEQ ID NO: 27)). Briefly, the PCR was performed with an initial denaturation at 95° C. for 10 min., followed by 28 cycles of denaturation at 95° C. for 30 sec, annealing at 65° C. for 30 sec, elongation at 72° C. for 45 sec and finally by a 10 min elongation at 72° C. The resulting PCR products were analyzed by standard agarose gel electrophoresis using a 1% agarose gel and visualizing the DNA with Ethidium bromide as described in Ausubel et al., 1992. Three transgenic lines (#103, #107 and #1010) were established by breeding heterozygous mice with C57BL/6JxCBA.

Results

As expected, initial characterization of the three lines revealed very large differences in levels of recombinant scce expression (see example 3). In line #1010, which has the highest hscce transcript levels, skin abnormalities were apparent, whereas in the two other lines no skin changes or other gross phenotypic deviations could be observed. For further detailed comparative studies of the #1010 transgenics one of the lines with apparently normal phenotype (#107) and non-transgenic littermates were included as controls. Macroscopic phenotypic changes in transgenic #1010 animals were noted as a loss of hair from a narrow zone around the eyes in mice 4–5 weeks of age. In older mice there was an apparent thinning of body hair in general, and a luster-less appearance of the coat. On the back the skin surface was sometimes covered with fine scales. From the age of 5–6 weeks and onwards several of these transgenic animals showed signs of itch with scratching, the frequency of which increased with time.

Diagnostic necropsies with routine histological analyses were carried out on transgenic mice of the #1010 and #107 C57BL/6JxCBA lines, and of littermate controls. Tissues examined were brain, cerebellum, intestines (duodenum/jejunum, ileum, colon, rectum), and skin. In some animals 3 weeks of age heart, liver, lung, salivary gland, spleen, thymus and thyroid were also examined. In littermate controls (for #1010: 3 weeks, n=5; 5 weeks, n=5; for #107 5 weeks, n=3) and transgenic mice of the #107 line (5 weeks n=3) no significant macro- or microscopic abnormalities were observed. In transgenic animals from line #1010 abnormalities were found in the skin, but in no other organs or tissues. In mice 3 weeks of age (i.e. before phenotypic changes could be observed by inspection of living animals) skin changes were found in all animals examined (n=4). These changes included mild to moderate epidermal hyperplasia and hyperkeratosis and a mild cellular inflammatory reaction with mixed leukocytes in the upper dermis. In animals 5 weeks of age (n=4) the skin abnormalities were of the same type but more pronounced with a marked acanthosis-like hyperplasia and a hyperkeratosis of the epidermis which was mainly orthokeratotic. In addition, the number of mast cells in the dermis was increased in some of the animals. Leukocyte invasion of the epidermis was occasionally found and then manifested as small groups of granulocytes within the thickened cornified layer, which at these sites was parakeratotic.

Example 3

Determining the Expression of scce-mRNA, SCCE Protein in Mice and Catalytically Active SCCE in SV40e-scce-Transgenic Mice.

Isolation of Tissues.

Tissue specimens were collected at different ages and immediately frozen and stored in liquid nitrogen until analyzed.

RNA Isolation and cDNA Synthesis and Real Time Quantitative PCR.

From 50–300 mg of the isolated tissues liver, skin, lung, brain, small intestine, colon, and ear, total RNA were prepared using RNA STAT-60™ (Tel-Test "B", Inc., Friendswood, Tex., USA) according to the manufacturer. 50 µg of each RNA preparation were DNase treated using RQ1 DNase (Promega, Madison, Wis., USA) according to Ausubel et al . About 1,6 µg total RNA from each tissue was used for cDNA synthesis. Three RNA samples from animals with same genetic background and tissue were mixed and cDNA synthesis was made using Superscript™ Preamplification System for First Strand cDNA Synthesis (Life Technologies, Inc. Gaithersburg, Md., USA) according to the manufacturer. The cDNA synthesis was primed using Oligo d(T)$_{12-18}$ primer. The synthesized cDNA were diluted 100× in water prior to real time quantification. Real time quantification was performed three times on each cDNA. Primer and probe for real time quantification of transgenic human SCCE were designed over exons four and five where the sequence between human and murine SCCE show little (less) homology. The forward primer (5'-GCGAACCCCCTGGAACAA-3') (SEQ ID NO: 28) covers the position 427–444 of the human cDNA sequence (ref. Hansson et al) in exon four. The reverse primer (5'-ACATCCACGCACATGAGGTCA-3') (SEQ ID NO: 29) covers the position 490–510 of the human cDNA sequence in exon five. The real time amplification probe (5'-CCTGTACTGTCTCCGGCTGGGGCACTACC-3') (SEQ ID NO; 30) covers the position 445–473 of the human cDNA sequence in exon four, and was labelled with the reporter fluorescent dye FAM in the 5'-end and the quencher fluorescent dye TAMRA in the 3'-end. The amplification of PCR products and real time detection were performed in ABI Prism 7700 Sequence Detection System (PE Applied Slosystems, Foster City Calif., USA). Amplification of a part of murine acidic ribosomal phosphoprotein P0 (ACC# X15267) was used as endogenous control for the real time quantitation studies. The relative quantitation was calculated according to the formula $2^{-\Delta\Delta T}$, where $\Delta C_T$ is the difference in $C_T$ values between the target and the endogenous control (User Bulletin #2, PE Applied Bicsystem).

SCCE-specific Polyclonal Antibodies.

Polyclonal antibodies to recombinant human SCCE were prepared and affinity purified as described by Sondell et al.(Sondell et al. 1996). These antibodies are reactive towards human SCCE and proSCCE, as well as murine SCCE.

Tissue Preparation, ELISA, Immunoblotting and Zymography.

Tissue extracts for ELISA were prepared by homogenization of 200–400 mg frozen tissue in 1 ml dH$_2$O containing a mixture of protease inhibitors (Complete TM Protease Inhibitor Cocktail Tablets cat. no. 1836153, Boehringer Mannheim, Germany), followed by centrifuging at 20 000×g for 30 min at 4° C. Protein concentrations was determined by reaction with bicinchoninic acid with bovine serum albumin as standard For SDS-polyacrylamide gel electrophoresis approximately 0.1 mg of mouse skin was homogenized in 10 ml of 1 M acetic add and extracted over night at 4° C. After clearing by centrifugation extracts were aliquoted, lyophilized, and resolubilized in electrophoresis sample buffer for zymography. SDS-polyacrylamide gel electrophoresis, zymography, and immunoblotting were carried out as described (Ekholm et al. 2000).

For ELISA polystyrene microtiter plates were coated with 100 µl of SCCE-specific rabbit polyclonal antibodies at a concentration of 7 µg/ml prepared in coating buffer (0.1 M Na$_2$CO$_3$, 0.02% NaN$_3$ (w/v), pH 9.6). After incubation over night at 4° C. on a wobbling table, the plate was washed once with washing buffer (10 mM NaH$_2$PO$_4$, 0.15 M NaCl, 0.05% (v/v) Tween 20, pH 7.2). Thereafter, 200 µl blocking buffer (10 mM NaH$_2$PO$_4$, 0.15 M NaCl, 0.1% (w/v) Bovine Serum Albumine (BSA), pH 7.2) was added to each well and the plate was incubated at 37° C. for 1 h. The plate was washed three times with washing buffer, 50 µl of sample (or standard) in dilution buffer (10 mM NaH$_2$PO$_4$, 0.15 M NaCl, 0.1% (w/v) BSA, 0.05% (v/v) Tween 20, pH 7.2) was added to each well and the plate was incubated for 1 h at 37° C. Plates were washed three times with washing buffer, and further prepared by adding 100 µl/well of SCCE-specific antibodies (7 µg/ml) labelled with alkaline phosphatatse Plates were incubated for 1 h at 37° C. before washing three times with washing buffer. Development was performed by addition of 100 µl freshly prepared substrate solution (2 tablets of phosphatase substrate (Sigma 104 phosphatase substrate tablets) dissolved in 10 ml 0.1 diethanol amine-HCl, 0.5 mM MgCl$_2$, pH 9.8). Plates were incubated in the dark for 30 min at room temperature. Finally, 25 µl stop solution was added to each well and the absorbance was read at 405 nm. For quantitation recombinant human pro-SCCE (Hansson et al) was used as standard.

Results

Real Time Quantification of Human SCCE Transcribed in Transgenic Mice.

In order to investigate if the difference in skin phenotype between #1010 ABD #107 transgenic lines expression of hscce mRNA in various tissues was analyzed by quantitative RT-PCR. The results are shown in FIG. 3A.

Six different tissues were analyzed. The analyses showed significantly higher expression of hscce in all tissues examined for transgenic mice of the #1010 line as compared to mice of the #107 line and non-transgenic littermates. The highest relative hscce mRNA levels were found in the intestines and lungs, but the difference in hscce expression between the two transgenic lines was most pronounced for skin, in which the relative level of hscce mRNA was about 24 times higher in #1010 mice than in #107 mice.

Elisa

Analyses of SCCE protein with ELISA (FIG. 4B) showed values close to or below the detection limit for tissues from transgenics of the #107 line and normal controls. In #1010 transgenics SCCE protein was readily detectable in several tissues including skin, intestines, and lung, the relative level (ng/mg) being highest in the skin.

Immunoblotting and Zymography

Immunoblotting with SCCE-specific antibodies corroborated the ELISA-results. In extracts of skin of control mice small amounts of a component with molecular mass similar to human SCCE was detected, whereas a component with the same relative molecular mass detected in high amounts in skin extracts from #1010 transgenic mice (FIG. 4A). Zymography in casein-containing acrylamide gels showed that the extracts of skin from #1010 transgenics contained a proteolytic enzyme with the same electrophoretic mobility as human SCCE. A corresponding enzyme could not be detected in control extracts (FIG. 4B; the amounts of active murine SCCE are too low to be detected under the experimental conditions used). These results suggest that a fraction of the human pro-SCCE produced in skin of #1010 transgenics is converted to proteolytically active enzyme. This was supported also by the immunoblotting experiments (FIG. 3A), where a component corresponding to active human SCCE was labelled with the antibodies. In addition to SCCE, the skin extracts of #1010 transgenics contained increased amounts of a proteolytic enzyme not related to SCCE. The nature of this enzyme is presently not known.

Conclusion

The expression of hscce in various tissues at the RNA level was higher in #1010 transgenic mice than in the #A107 transgenic mice. The difference between transgenics from the two lines was even more pronounced as regards expression of SCCE-protein. In skin of #1010 transgenic mice high amounts of SCCE protein could be detected with immunoblotting. The majority of this protein appeared to be pro-SCCE, but also active SCCE could be detected in increased amounts.

Example 4
Scce-transgenic Mice as Models for Studies of Inflammatory Skin Diseases and Itch Three male transgenic #1010 mice were mated with wild type C57BL/63 females, resulting in 6 litters with a total of 40 mice. Of these 19 (8 transgenics) were sacrificed at the age of 7–8 weeks and 21 (11 transgenics) were followed to the age of 13–14 weeks. In the latter group scratch movements with the legs were quantified.

Macroscopic phenotypic changes in transgenic #1010 animals were noted as a loss of hair from a narrow zone around the eyes in mice 4–5 weeks of age. In older mice there was an apparent thinning of body hair in general, and a luster-less appearance of the coat. On the back the skin surface was sometimes covered with fine scales. From the age of 5–6 weeks and onwards several of these transgenic animals showed signs of itch with scratching, the frequency of which increased with time.

Itching Behavior

Figure 5:
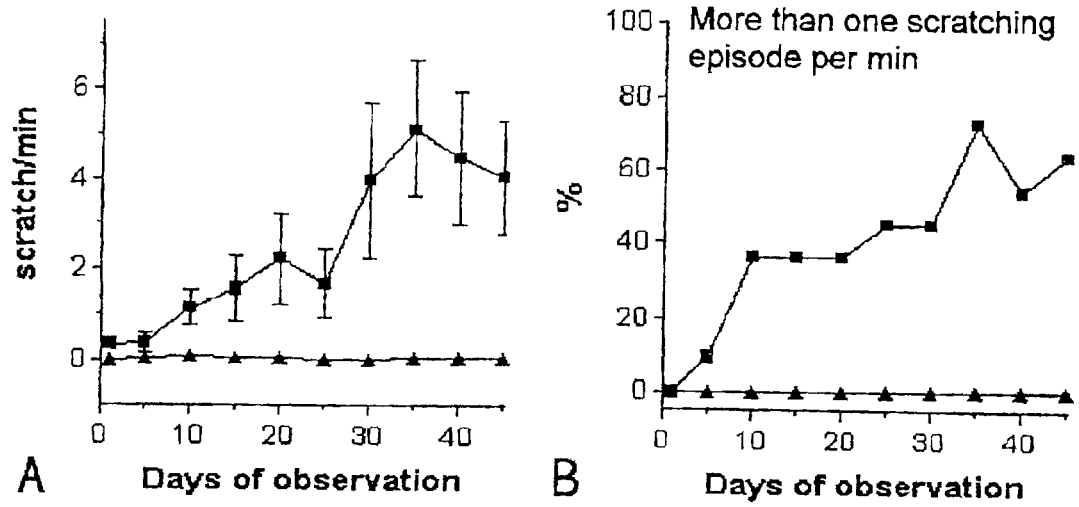

Of the 11 transgenic mice followed for 13–14 weeks 8 animals (73%) showed signs of itch (at least one period of scratching with hind or fore paws per minute) at the age of 10–11 weeks. The frequency of scratching varied among the observed animals; whereas some animals showed weak or moderate signs of itch, other animals spent most of their time scratching (FIG. 5). Up to the age of 3 weeks there was no statistically significant difference in weight between transgenic and normal animals. With increasing age there was a tendency towards lower weights among transgenics. At the age of 14–15 weeks there was a 7–10% reduction in weight in transgenics as compared to wild-type litter mates (mean for males 27.0 gm versus 30.0 gm; $p=0.022$; mean for females 21.7 gm versus 23.5 gm; $p=0.033$).

Histological Analysis

For histology and immunohistochemistry (Ekholm et al. 1998 and Sondell et al. 1996) samples were either formaldehyde fixed and paraffin embedded according to routine protocols or frozen after fixation for 2 h in formaldehyde.

Upon sacrifice of the animals tissues (dorsal skin, large and small intestines, and lung) were prepared for microscopic analyses. The preliminary microscopic examination of routinely processed skin samples was carried out blindly (the examiner was not informed about genotype or scratching behavior). In all cases but one, transgenics could be differed from wild type controls, the most prominent difference being the thickened epidermis in transgenic animals. Epidermal thickness was 55 μm (SD=21 μm; n=19) for transgenic animals, and 15 μm (SD=2.6 μm; n=21; $p<0.001$) for controls. There was no statistically significant difference in epidermal thickness between younger (7–8 weeks) and older (13–14 weeks) transgenic animals. Other prominent and frequent histological findings in skin of transgenic animals as compared to controls (FIGS. 6 A–B) were a marked hyperkeratosis, an increased cellularity of the dermal part of the skin, and increased epithelial thickness of adnexal structures (hair follicle walls and sebaceous glands and ducts). The increase in number of cells in the connective tissue was only partially due to lymphocytes and granulocytes; there appeared to be an increase also in the number of fibroblasts and/or histlocyte-like cells. Tolouidine blue staining showed increased number of dermal mast cells in some transgenic animals (results not shown). In routine stained sections no differences could be found between transgenics and controls for any of the other organs examined (results not shown).

Immunohistochemistry

Immunohistologic analyses of skin samples from #1010 transgenic animals and littermate controls with SCCE-specific antibodies showed strong labelling of keratinocytes in suprabasal parts of interfollicular epidermis in transgenics, including the thickened cornified layer. In hair follicles and sebaceous ducts only luminal parts, including the cornified lining of follicles and ducts, were stained (FIG. 6C). This was in marked contrast to basal cells of interfollicular epidermis and the major parts of hair follicles and sebaceous ducts and glands, where no or very weak labelling by the antibodies was seen. In controls there was a relatively weak labelling of a narrow zone of interfollicular epidermis close to the transition to the stratum corneum, of the stratum corneum, and of luminal parts of hair follicles (FIG. 6D). This pattern was similar to that previously described for normal human epidermis (Ekholm et al 1998). With immunofluorescence microscopy on formaldehyde fixed frozen samples similar results (not shown) were obtained.

In the intestines SCCE-specific labelling was seen only in transgenics and in irregularly distributed epithelial cells. Stained cells were more numerous at the tips of villi in the small intestine and in the luminal parts of colonic epithelium. In the lungs of transgenics apical parts of bronchiolar epithelia cells were weakly labelled. At higher antibody concentrations there appeared to be a diffuse labelling also of the alveolar epithelium (results for intestines and lung not shown).

Comparison with Diseased Human Skin.

Figure 6:
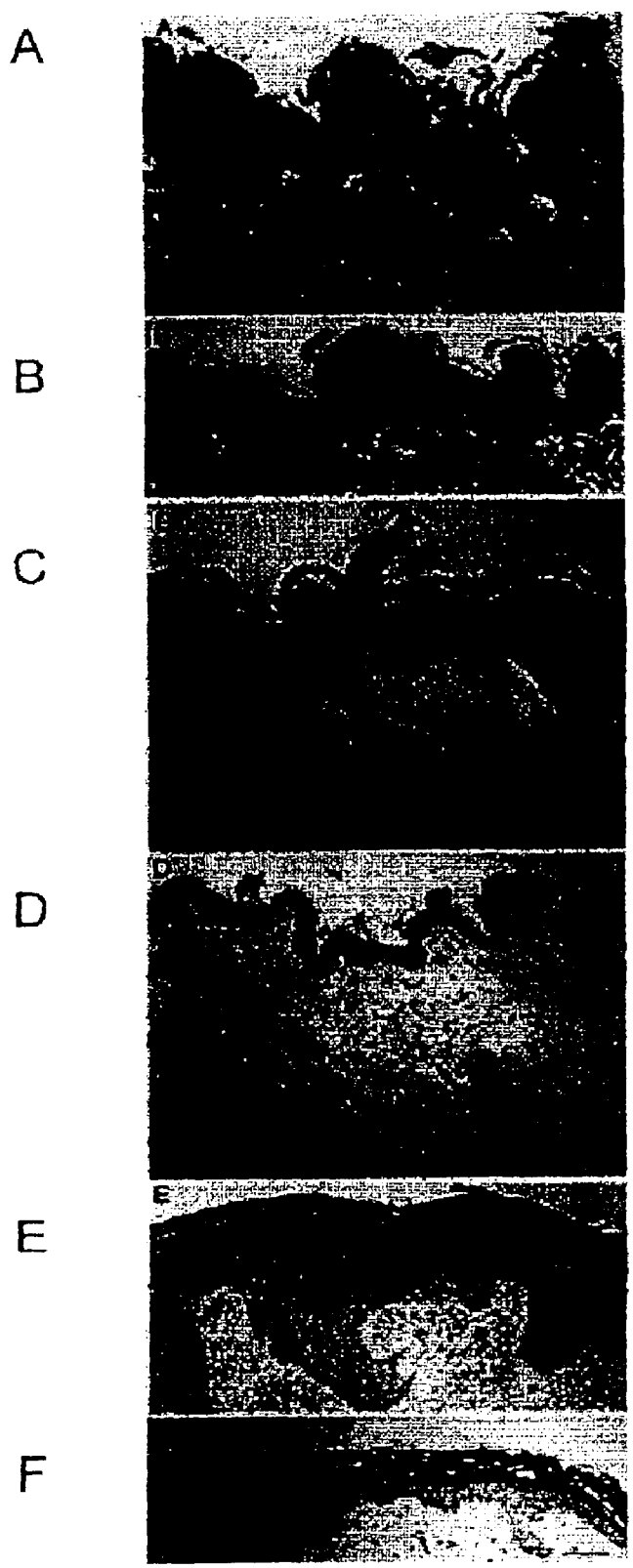

Skin biopsies from human volunteers and patients were taken after informed consent and with the approval of the Human research ethics committee, Umeå University. Biopsies were taken from chronic eczematous lesions on the flexural sides of lower arms of five adults with atopic dermatitis and processed for microscopy as above. Biopsies from corresponding sites were obtained from volunteers. In routine stained sections (not shown) the lesions showed, as expected, marked acanthosis, hyperkeratosis, and a sparse dermal infiltrate consisting mainly of lymphocytes. Immunohistology with SCCE-specific antibodies showed a drastic increase in the number of labelled suprabasal cell layers as compared to controls (FIGS. 6 E–F). As regards the acanthosis, hyperkeratosis, and pattern of SCCE-specific staining the differences seen between lesional and normal skin were strikingly similar to those seen between skin of #1010 transgenic mice and controls.

Example 5
Scce-transgenic Mice for Testing of Antiprurtic Agents

Figure 7:
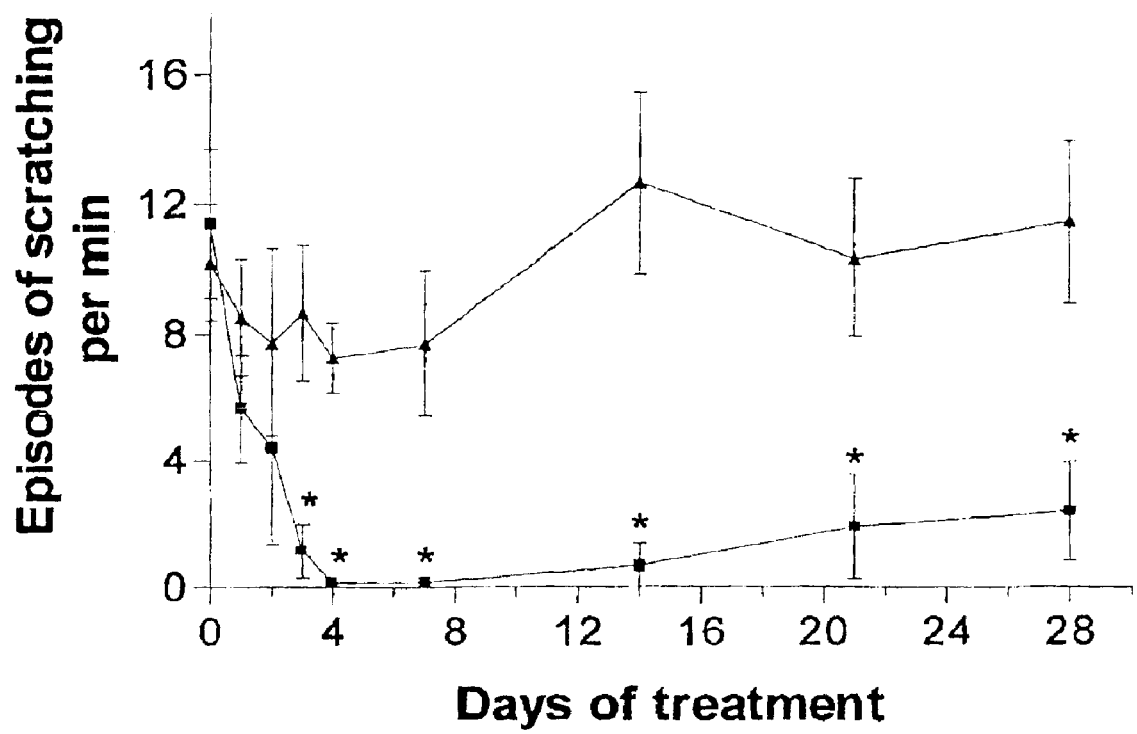

Transgenic mice, 18–22 weeks of age, mean weight 24.2 g, were given subcutaneous injections of either 250 μg of the glucocorticoid triamcinolone acetonide in a total volume of 100 μl on day 0, and 100 μg triamcinolone acetonide in a total volume of 100 μl on days 7, 14 and 21, or 100 μl of physiological saline at the same time points. Episodes of scratching were counted in the morning and injections were given in the afternoon. To prepare solutions for injections 25 μl or 10 μl or Kencort-T™ suspension, 10 mg/ml (Bristol-Myers Squibb), was mixed with 75 μl or 90 μl of physiological saline. The results are shown in FIG. 7. Triamcinolone acetonide was highly efficient in diminishing scratching.

Figure 8:
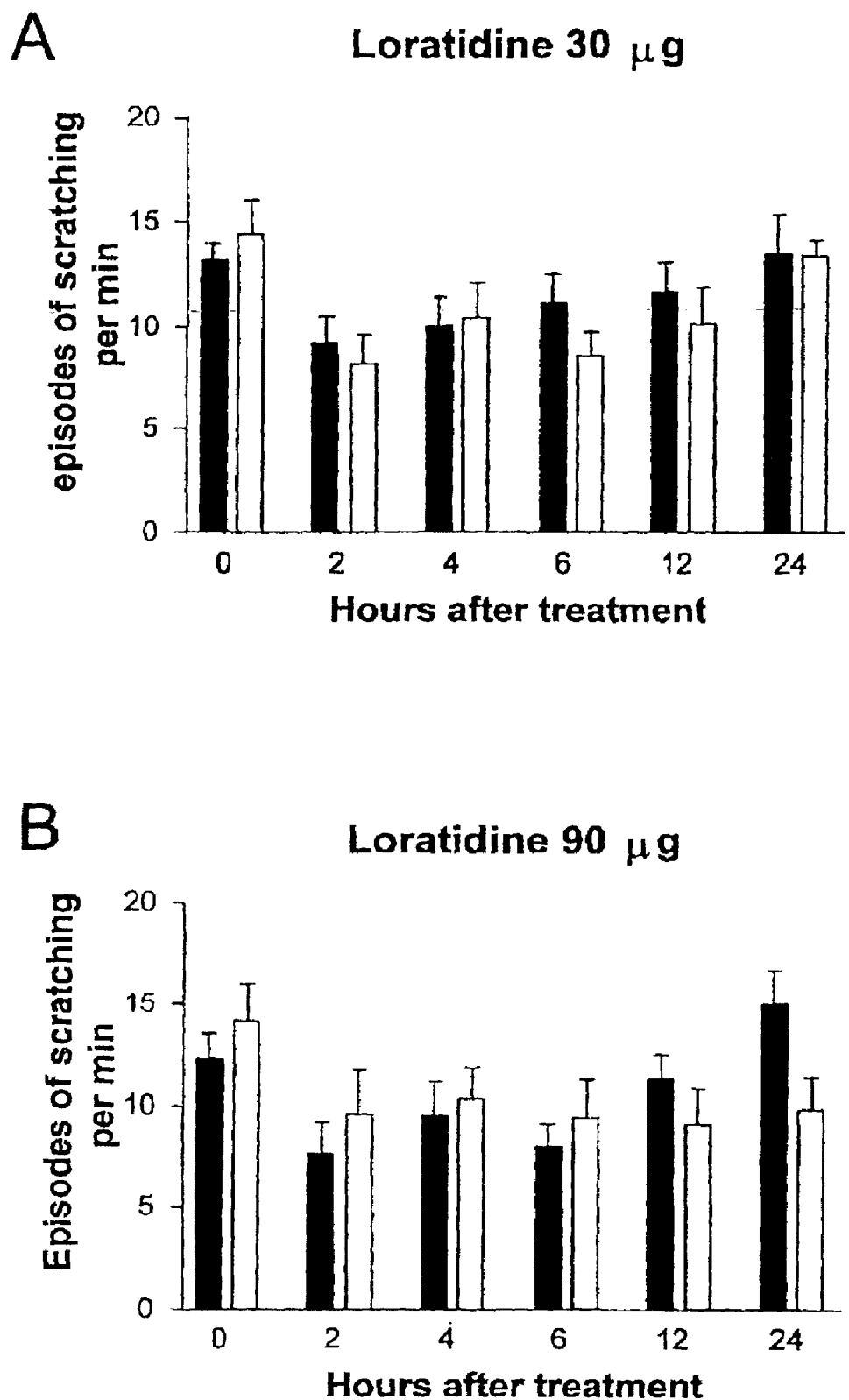

Transgenic mice 20–21 weeks of age, mean weight 24.5 mg, were given either loratidine in a total volume of 100 μl, or 100 μl of a control solution by means of tube feeding. Episodes of scratching were counted immediately before feeding (0 hours), and then at time points as indicated. Feeding solutions were prepared by mixing either 30 μl of loratidine 1 mg/ml, sucrose 600 mg/ml (Clarityn mixture™, Schering-Plough), or, for control solutions, 30 μl of sucrose 600 mg/ml, with 70 μl of physiological saline. The results are shown in FIG. 8A. The same mice were then treated 7 days later with 90 µl of loratidine mixture of sucrose solution mixed with 10 µl of physiological saline. The results are shown in FIG. 8B. As seen from FIGS. 8A and 8B there was no significant difference in frequency of scratching between treatment group and control group. This indicates that the itching behavior of the SCCE mouse is not relieved by treatment with an antihistamine.

The two experiments show that scce-transgenic mice can be used for evaluation of drugs with potential effects on itch (anti-pruritic drugs). The glucocorticoid triamcinolone acetonide appeared to be highly effective in relieving itch, whereas the antihistamine loratidine had no statistically significant antipruritic effect.

It thus appears that the pruritus in SCCE-transgenic mice respond to treatment with a glucocorticoid but not to treatment with an antihistamine. A similar situation can be found for human patients suffering from pruritus associated with e.g. atopic dermatitis, eczema, and psoriasis.

Example 6

Determination of Nucleotide Sequences of Homologues to hscce-cDNA from Cow, Rat and Pig.

Skin biopsies from cow, pig and rat were obtained, immediately frozen in liquid nitrogen and homogenized, using a Mikro-Dismembranator U (B.Braun Biotech International GmbH, Melsungen, Germany) at 2000 rpm for 45 s. RNA was isolated using 1 ml of Trizol Reagent (Life Technologies AB, Täby, Sweden) according to the manufacturers Instructions, DNase treated, extracted with Phenol:HCl$_3$, and precipitated with LiCl according to the Boehringer Mannheim protocol (Nonradioactive in Situ Hybridization application Manual, Boehringer Mannheim, Mannheim, Germany).

RT-PCR was performed as described (Lindström et al. with oligo d(T)$_{16}$ primers (Perkin Elmer, Foster City, Calif., USA) in the RT reaction. In each RT reaction 100 ng of total RNA was used.

For PCR five primers were designed from conserved sequences found in hscce and mscce cDNA resulting in primers mS3, 698,696,H2 and mS4 (Table 4). PCR products were cloned into pCR II vector using the TOPO TA cloning kit (Invitrogen/NOVEX, Groeningen, The Netherlands) as recommended by the manufacturers. Plasmid DNA was isolated using the QIAprep Spin Miniprep Kit (Qiagen, Chatsworth, Calif.). Nucleotide sequencing was performed using the DYEnamic ET Terminator Cycle Sequencing Kit (Amersham Pharmacia Biotech Sverige, Uppsala, Sweden) and an ABI377 automated DNA sequencer (Perkin-Elmer).

To obtain the 5'cDNA end the SMART Race cDNA Amplification Kit (Ciontech Laboratories, Inc., Palo Alto, Calif.) was used according to the manufacturers instructions. Species specific primers were designed from the cDNA sequences obtained in previous steps (Table 4).

TABLE 4

Oligomer primers used in RT-PCR, 5'-RACE and nested 5'-RACE Oligomers a-e were designed from conserved sequences found when comparing SCCE and mSCCE cDNA sequences. Positions are derived from the mSCCE cDNA (Backman er al., Oligomers f-j were designed based on nucleotide sequencing data from the preceding species specific cloning reactions.

| Oligomer | Sequence, 5' to 3' | |
|---|---|---|
| a) mS3 | CAAGGAGAAAGGATTATAGATGGCT | (SEQ ID NO:31) |
| b) 698 | AAGGCTCCGCACCCATGGCAG | (SEQ ID NO:32) |
| c) 696 | TGCAATGGTGACTCAGGGGGGCCCTT | (SEQ ID NO:33) |
| d) H2 | GACCCAGGCGTCTACACTCAAGT | (SEQ ID NO:34) |
| e) mS4 | GAGACCATGAAAACCCATCGCTAAC | (SEQ ID NO:35) |
| f) KO0905 | TGACTTTCTTCACACTGGACGACAGC | (SEQ ID NO:36) |
| g) GR0905 | CTTCACACTGGCTGATAGCCTGGCCG | (SEQ ID NO:37) |
| h) Ngr | CAGGGTGGCGGAATGACCTCATGGCCCT | (SEQ ID NO:38) |
| i) RÅ1016 | CTACTCCACAAGGACCCATGTCAATGAC | (SEQ ID NO:39) |
| j) nRÅ 1016 | GCTGTGTGCTGGCATTCCCGACTCTAAG | (SEQ ID NO:40) |

First strand cDNA was prepared from total RNA using SMART II oligonucleotide (5'-AAGCAGTGGTAACAACGCAGAGTACGCGGG-3') (SEQ ID NO: 41) and 5'-RACE cDNA synthesis primer (5'-(T)$_{25}$ N$_{-1}$N-3') (N=A, C, G, or T; N. A, G. or C) (SEQ ID NO: 42). 5'-RACE was performed using Universal primer mix (UPM) containing Long (0.02 µM) (5'-CTAATACGACTCACTATAGGGCAAGCAGTGGTAAC AACGCAGAGT-3) (SEQ ID NO: 43) and Short (1 µM) (5'-CTAATACGACTCACTATAGGGCC-3') (SEQ ID NO; 44) universal primer and a specific primer for each species (KO 0905, GR 0905 and RÅ 1016). Cyclic parameters for the PCR reaction were adapted from the manufacturers recommendations for a Perkin-Elmer DNA Thermal Cycler 480 but with 25 cycles in the last step. 5'-RACE PCR products from reactions with specific primers for pig and rat were subjected to nested PCR using Nested Universal Primer (NUP) (5'-AAGCAGTGGTAACAACGCAGAGT-3') (SEQ ID NO: 45) and nested specific primers for pig (nGR0905) and rat (nRÅ1016) respectively. The nested PCR reactions were performed according to the manufacturers instructions with 20 cycles of amplification. Products from 5'-RACE and nested 5'-RACE were checked on agarose gel. For characterization products were cloned and sequenced as described above. The results are shown in table 5 as deduced amino acid sequences. Table 6 show the calculated similarities of the active enzyme starting with the sequence IIDG. Sequences for human (Hansson et al., 1994) and mouse SCCE (Bäckman et al., 1999) are included for comparison.

The rat SCCE sequence shown in table 5 and in SEQ ID NO: 49 can not be found in the GenBank database which indicate that it does not correspond to any of the already known rat kallikreins or kallikrein like proteins.

TABLE 5

Alignment of the deduced amino acid sequences of SCCE from five species. The sequences for cow, pig, and rat are not complete in the C-terminal parts.

```
seq2
----MTTPLVILLLTFALGSVA QEDQGNKSGEKIIDGVPCPRGSQP    56
                       WQVALLKGSQLHCG
seq3
MARPLLPPRLILLLSLALGSAA QEGQ-DKSGEKIIDGVPCPGGSRP    59
                       WQVALLKGNQLHCG
seq1
MARSLLLPLQILLLSLALETAG EEAQ----GDKIIDGAPCARGSHP    56
                       WQVALLSGNQLHCG
seq4
-MGVWLLSLLTVLLSLALETAG Q-------GERIIDGYKCKEGSHP    52
                       WQVALLKGDQLHCG
seq5
-MGVWLLSLITVLLSLALETAG Q-------GERIIDGIKCKEGSHP    52
                       WQVALLKGNQLHCG seq2
GVLLNEQWVLTAAHCMN-EYNVHMGSVRLVGG--QKIKATRSFRHPG   112
                       YSTQTHANDLMLV
seq3
GVLVNQQWVLTAAHCMMNDYNVHLGSDRLDDRKGQKIRAMRSFRHPG   119
                       YSTQTHVNDLMLV
seq1
GVLVNERWVLTAAHCKMNEYTVHLGSDTLGDRRAQRIKASKSFRHPG   116
                       YSTQTHVNDLMLV
seq4
GVLVGESWVLTAAHCKMGQYTVHLGSDKIEDQSAQRIKASRSFRHPG   112
                       YSTRTHVNDIMLV
seq5
GVLVDKYWVLTAAHCKMGQYQVQLGSDKIGDQSAQKIKATKSFRHPG   112
                       YSTKTHVNDIMLV seq2
KLNGRAKLSSSVKKVNLPSHCDPPGTMCTVSGWGTTTSPDVTFPGQL   172
                       MCTDVKLISPQDC
seq3
KLSRPARLSASVKKVNLPSRCEPPGTTCTVSGWGTTTSPDVTFPADL   179
                       MCTDVKLISSQDC
seq1
KLNSQARLSSMVKKVRLPSRCEPPGTTCTVSGWGTTTSPDVTFPSDL   176
                       MCVDVKLISPQDC
seq4
KMDKPVKMSDKVQKVKLPDHCEPPGTLCTVSGWGTTTSPDVTFPSDL   171
                       MCSDVKLISSQEC
seq5
RLDEPVKMSSKVEAVQLPEHCEPPGTSCTVSGWGTTTSPDVTFPSDL   172
                       MCSDVKLISSREC seq2
RKVYKDLLGDSMLCAGIPNSRTNACNGDSGGPLMCKGTLQGVVSWGS   232
                       FPCGQPNDPGVYT
seq3
KKVYKDLLGSSMLCAGIPNSKTNACNGDSGGPLVCKGTLQGLVSWGT   239
                       FPCGQPNDPGVYT
seq1
TKVYKDLLENSMLCAGIPDSKKNACNGDSGGPLVCRGTLQGLVSWGT   236
                       FPCGQPNDPGVYT
seq4
KKVYKDLLGKTMLCAGIPDSKTNTCNGDSGGPLVCNDTLQGLVSWGT   225
                       YPCGQPN------
seq5
KKVYKDLLGKTMLCAGIPDSKTNTCNGDSGGPLVCNDTLQGLASRGT   232
                       YPCGQPNDPGVYT seq2
QVCKYVNWIK------- 242
seq3
QVCKYIDWIN------- 249
seq1
QVCKFTKWINDTMKKHR 253
seq4
-----------------
seq5
QVCKYKRWVMETMKTHR 249
```

Seq 2 (cow) in the figure is SEQ ID NO:46,
Seq 3 (pig) in the figure is SEQ ID NO:47,
Seq 1 (homo) in the figure is SEQ ID NO:48,
Seq 4 (rat) in the figure is SEQ ID NO:49 and
Seq 5 (mouse) in the figure is SEQ ID NO:50.

TABLE 6

Calculated similarities of the active enzymes.

| species compared | calculated similarity* |
|---|---|
| Mouse-human | 75% |
| Rat-human | 77% |
| Pig-human | 77% |
| Cow-human | 76% |
| Rat-mouse | 88% |
| Cow-mouse | 69% |
| Pig-mouse | 69% |

*The comparisons of active enzymes are starting with the sequence IIDG etc.

REFERENCES

Ausubel et al. (1992). Current protocols in Molecular Biology. John Wiley & Sons Brattsand, M. & Egeirud, T. Purification, molecular cloning, and expression of a human stratum corneum trypsin-like serine protease with possible function in desquamation. 3 Biol Chem 274, 30033–30040 (1999).

Bäckman, A., Stranden, P., Brattsand, M., Hansson, L. & Egelrud, T. Molecular cloning and tissue expression of the murine analog to human stratum corneum chymotryptic enzyme. *J Invest Dermatol* 113, 152–155 (1999).

Chavanas, S. et al. Mutations in SPINKS, encoding a serine protease inhibitor, cause Netherton syndrome. *Nat Genet* 25, 141–142 (2000).

Diamandis, E. P., Yousef, G. M., Liu-Ying, L., Magkiara, A. & Oblezu, C. V. The New Hurman Kallikrein Gene Family—Implications in Carcinogenesis. *Trends in Endocrinology and Metabolism* 11, 54–60 (2000).

Ekholm, E. & Egelrud, T. Stratum corneum chymotryptic enzyme in psoriasis. *Arch Dermatol Res* 291, 195–200 (1999).

Ekholm, E. & Egelrud, T. The expression of stratum corneum chymotryptic enzyme in human anagen hair follicles: further evidence for its involvement in desquamation-like processes. *Br J Dermatol* 139, 585–590 (1998).

Ekholm, I. E., Brattsand, M. & Egelrud, T. Stratum corneum tryptic enzyme in normal epidermis: a missing link in the desquamation process? *J Invest Dermatol* 114, 56–63 (2000).

Hansson, L. et al. Cloning, expression, and characterization of stratum corneum chymotryptic enzyme. A skin-specific human serine proteinase. *J Biol Chem* 269, 19420–19426 (1994).

Hogan, B., Constanini, F. & Lazy, E. 1986 *In Manipulating the mouse embryo: A Laboratory Manual*. Cold Spring Harbor, N.Y., Cold Spring Laboratory Press. (Cold Spring Laboratory Press, Cold Spring Harbor N.Y., 1986).

Hägermark, D., Rajka, G. & Berqvist, U. Experimental itch in human skin elicited by rat mast cell chymase. *Acta Derm Venereol* (Stockh) 52, 125–128 (1972).

Hägermark, O. Studies on experimental itch induced by kallikrein and bradykinin. *Acta Derm Venereal* (Stockh) 54, 397–400 (1974).

Kroon, E., MacDonal, R. J. & Hammer, R. E. The transcriptional regulatory strategy of the rat tissue kallikrein gene family. *Genes and Function* 1, 309–310 (1997).

Lindström P., Bergh A., Holm I., Damber J. E. Expression of transforming growth factor-beta 1 in rat ventral prostate and Dunning R3327 PAP prostate tumor after castration and estrogen treatment. Prostate 29, 209–218 (1996).

Lusky, M. and Botchan M. Inhibition of sv40 replication in simian cells by specific pBR322 DNA sequences. *Nature*, 293, 79–81 (1981)

Sambrook et al. (1989) Molecular Cloning: A laboratory Manual, 2nd Ed., Cold Spring Harbor Laboratory, Cold Spring Harbor, N.Y. USA Sondell, B., Thomell, L. E. & Egelrud, T. Evidence that stratum corneum chymotryptic enzyme is transported to the stratum corneum extracellular space via lamellar bodies. *J Invest Dermatol* 104, 819–823 (1995).

Sondell, B., Dyberg, P., Anneroth, G. K., Ostman, P. O & Egetrud, T. Association between expression of stratum corneum chymotryptic enzyme and pathological keratinization in human oral mucosa. *Acta Derm Venereol (Stockh)* 76, 177–181 (1996).

Vassar et al (1989) Tissue-specific and differentiation-specific expression of a human K14 keratin gene in transgenic mice. Proc Natl Acad Sci U S A.86, 1563–7.

What is claimed is:

1. A transgenic mouse, having integrated within its genome a nucleotide sequence (SCCE-construct) comprising a heterologous nucleotide sequence coding for a human stratum corneum chymotryptic enzyme (SCCE), operably linked to a SV40 early promoter that drives expression of said heterologous nucleotide sequence in skin, wherein the mouse exhibits epidermal hyperplasia and hyperkeratosis and a mild cellular inflammatory reaction of the skin.

2. A transgenic mouse according to claim 1 wherein said operably linked SV40 early promoter drives expression of scce in epidermis.

3. A transgenic mouse according to claim 1, wherein the DNA sequence codes for the human SCCE corresponding to amino acid no. 23 through no. 253 of the amino acid sequence shown in SEQ ID NO. 2.

4. A tranagenic mouse according to claim 1, wherein the DNA sequence codes for the human SCCE corresponding to amino acid no. 30 through no. 253 of the amino acid sequence shown in SQ ID NO. 2.

5. A tranagenic mouse according to claim 1, wherein the DNA sequence codes for the human SCCE shown in SEQ ID NO. 2.

6. A transgenic mouse according to claim 1, wherein the heterologous nucleotide sequence is SEQ ID NO:1.

7. A method for making a transgenic mouse according to claim 1, the method comprising (a) constructing and amplifying said heterologous nucleotide sequence, (b) introducing said heterologous nucleotide sequence into a cell from a mouse, where said cell is selected from the group consisting of a mouse ovum, a mouse embryonic cell, and a mouse embryonic stem cell.

(c) using said cell or the progeny of said cell to create a number of putative transgenic mice, and (d) selecting said mouse having said heterologous nucleotide sequence integrated within its genome.

8. A method for making a transgenic mouse according to claim 7 wherein said operably linked promoter drives expression of scce in epidermis.

9. A method according to claim 7 comprising introducing the SCCE-construct into an ovum or embryo of the mouse.

10. A method according to claim 7 comprising microinjecting the SCCE-construct into embryonal stem cells of the mouse.

11. A method according to claim 7 comprising microinjecting the SCCE-construct into C57BL/6JxCBA-f2 mouse ova or embryos.

12. A method according to claim 7 comprising introduction of the SCCE-construct into C57BL/6JxCBA-f2 mouse ova or embryos and breeding the resulting mice with C57BL/6JxCBA or with C57BL/6J to obtain transgenic progeny and stable mouse lines.

13. A method of identifying a compound or composition effective for the prevention or treatment of epidermal hyperkeratosis, acanthosis, epidermal inflammation, dermal inflammation and pruritus, the method comprising (a) administering a compound or composition to a transgenic mouse according to claim 1, (b) evaluating the appearance of the skin and/or the behavior of a mouse treated according to step (a), and (c) comparing the appearance of the skin and/or the behavior of a treated mouse with an untreated control mammal, (d) identifying the compound or composition as being effective for the prevention or treatment of epidermal hyperkeratosis, acanthosis, epidermal inflammation, dermal inflammation and pruritus.

14. A method according to claim 13 of identifying a compound or composition effective for the prevention or treatment of epidermal hyperkeratosis.

15. The method of claim 7 in which said introduction is by electroporation, transfection, microinjection or viral infection.

16. The method of claim 7 in which said introduction is by microinjection.

17. The method of claim 16 in which the microinjection is into a mouse ovum.

* * * * *